US008642658B2

(12) United States Patent
Radzioch et al.

(10) Patent No.: US 8,642,658 B2
(45) Date of Patent: Feb. 4, 2014

(54) TREATMENT OF NEURAL DISEASES OR CONDITIONS

(75) Inventors: Danuta Radzioch, St-Laurent (CA); Samuel David, Dorval (CA); Ruben Lopez-Vales, Manresa (CH); Thomas Skinner, Halifax (CA)

(73) Assignee: Royal Institution for the Advancement of Learning/McGill University, Montreal, Quebec (CA)

( * ) Notice: Subject to any disclaimer, the term of this patent is extended or adjusted under 35 U.S.C. 154(b) by 506 days.

(21) Appl. No.: 12/918,787

(22) PCT Filed: Feb. 20, 2009

(86) PCT No.: PCT/CA2009/000208
§ 371 (c)(1),
(2), (4) Date: Aug. 20, 2010

(87) PCT Pub. No.: WO2009/103166
PCT Pub. Date: Aug. 27, 2009

(65) Prior Publication Data
US 2010/0331417 A1    Dec. 30, 2010

Related U.S. Application Data

(60) Provisional application No. 61/030,354, filed on Feb. 21, 2008.

(51) Int. Cl.
*A61K 31/16*    (2006.01)
*C07C 233/00*    (2006.01)

(52) U.S. Cl.
USPC .......................................... 514/613; 564/123

(58) Field of Classification Search
None
See application file for complete search history.

(56) References Cited

U.S. PATENT DOCUMENTS

| 4,874,795 | A | 10/1989 | Yesair |
| 5,516,792 | A | 5/1996 | Curley, Jr. et al. |
| 5,574,177 | A | 11/1996 | Curley, Jr. et al. |
| 5,599,953 | A | 2/1997 | Curley, Jr. et al. |
| 5,663,377 | A | 9/1997 | Curley, Jr. et al. |
| 5,972,911 | A | 10/1999 | Yesair |
| 2005/0106216 | A1 | 5/2005 | Maurer et al. |
| 2006/0264514 | A1 | 11/2006 | Formelli |

FOREIGN PATENT DOCUMENTS

| CA | 2596759 | 8/2006 |
| JP | 2002293746 | 10/2002 |
| WO | WO 02/058689 | 8/2002 |
| WO | WO 2004/069203 | 8/2004 |
| WO | WO 2007/068116 | 6/2007 |
| WO | WO 2007/104030 | 9/2007 |
| WO | WO 2007/115134 | 10/2007 |
| WO | WO 2007/136636 | 11/2007 |

OTHER PUBLICATIONS

Sabichi et al., "Retinoid Receptor-Dependent and Independent Biological Activities of Novel Fenretinide Analogues and Metabolites," Clinical Cancer Research, 2003, 9, pp. 4606-4613.*
Toborek et al., "Arachidonic Acid Induced Oxidative Injury to Cultured Spinal Cord Neurons," Journal of Neurochemistry, 1999, 73(2) pp. 684-692.*
Anding et al., "The Unhydrolyzable Fenretinide Analogue 4-Hydroxybenzylretinone Induces the Proapoptotic Genes *GADD153* (*CHOP*) and *Bcl-2-Binding Component 3* (*PUMA*) and Apoptosis that Is Caspase-Dependent and Independent of the Retinoic Acid Receptor," *Cancer Research*, 67(13): 6270-6277, 2007.
Basso et al., "Basso Mouse Scale for Locomotion Detects Differences in Recovery after Spinal Cord Injury in Five Common Mouse Strains," *Journal of Neurotrauma*, 23(5): 635-659, 2006.
Bhatnagar et al., "Growth Suppression of Human Breast Carcinoma Cells in Culture by N-(4-Hydroxyphenyl) Retinamide and Its Glucuronide and Through Synergism with Glucarate," *Biochemical Pharmacology*, 41(10): 1471-1477, 1991.
Charles et al., "Taxol-induced ceramide generation and apoptosis in human breast cancer cells," *Cancer Chemother Pharmacol*, 47: 444-450, 2001.
Costa et al., "Retinoids in Cancer Chemoprevention. Clinical Trials with the Synthetic Analogue Fenretinide," *Ann. NY Acad. Sci.* 768: 148-162, 1995.
Crawford et al., "The Potential Role for Arachidonic and Docosahexaenoic Acids in Protection Against Some Central Nervous System Injuries in Preterm Infants," *Lipids*, 38(4): 303-315, 2003.
De Sanctis, Juan B., "Differences in the enzymatic hydrolysis of a marine lipid concentrate MaxEPA in comparison with Intralipid," *Med. Sci. Res.*, 19: 325-326, 1991.
Folch et al., "A Simple Method for the Isolation and Purification of Total Lipides from Animal Tissues," *J. Biol. Chem.*, 226: 497-509, 1957.
Garaventa et al., "Phase I Trial and Pharmacokinetics of Fenretinide in Children with Neuroblastoma," *Clinical Cancer Research*, 9: 2032-2039, 2003.
Ghasemlou et al., "Tissue displacement and impact force are important contributors to outcome after spinal cord contusion injury," *Experimental Neurology*, 196: 9-17, 2005.
Guilbault et al., "Fenretinide Corrects Newly Found Ceramide Deficiency in Cystic Fibrosis," *American Journal of Respiratory Cell and Molecular Biology*, 38:47-56, 2008.
Hensley et al., "On the Relation of Oxidative Stress to Neuroinflammation: Lessons Learned from the G93A-SOD1 Mouse Model of Amyotrophic Lateral Sclerosis," *Antioxidants & Redox Signaling*, 8(11-12): 2075-2087, 2006.
Hunter et al., "Retinoic acid stimulates neurite outgrowth in the amphibian spinal cord," *Proc. Natl, Acad. Sci. USA*, 88: 3666-3670, 1991.
International Search Report and Written Opinion, PCT App. PCT/CA2009/000208, 16 pages (Jun. 10, 2009).
Jones et al., "Inflammatory-Mediated Injury and Repair in the Traumatically Injured Spinal Cord," *Current Pharmaceutical Design*, 11: 1223-1236, 2005.

(Continued)

*Primary Examiner* — Sreeni Padmanabhan
*Assistant Examiner* — Jody Karol
(74) *Attorney, Agent, or Firm* — Klarquist Sparkman, LLP

(57) ABSTRACT

Compounds, methods, uses, compositions, kits and packages for the prevention and/or treatment of neural injury or a neurodegenerative disease, based on the use of a retinoic acid derivative, such as fenretinide, and/or analogs, derivatives, pro-drugs, precursors thereof, and/or salts thereof, are described.

14 Claims, 22 Drawing Sheets

(56) References Cited

OTHER PUBLICATIONS

Lippman et al., "Randomized Phase III Intergroup Trial of Isotretinoin to Prevent Second Primary Tumors in Stage I Non-Small-Cell Lung Cancer," *Journal of the National Cancer Institute*, 93(8): 605-618, 2001.

Maden, Malcolm, "Retinoic acid in the development, regeneration and maintenance of the nervous system," *Nature Reviews Neuroscience*, 8: 755-765, 2007.

Mey et al., "Retinoic Acid Signaling in the Nervous System of Adult Vertebrates," *The Neuroscientist*, 10(5): 409-421. 2004.

Ponthan et al., "Evaluation of anti-tumour effects of oral fenretinide (4-HPR) in rats with human neuroblastoma xenografts," *Oncol. Rep.*, 10(5): 1587-1592, 2003.

Puduvalli et al., "Fenretinide Activates Caspases and Induces Apoptosis in Gliomas," *Clinical Cancer Research*, 5: 2230-2235, 1999.

Rao et al., "Effect of retinoid analogues on mammary cancer in transgenic mice with *c-neu* breast cancer oncogene," *Breast Cancer Research and Treatment*, 48: 265-271, 1998.

Reynolds et al., "Retinoid Therapy of Childhood Cancer," *Hematol. Oncol. Clin. North Am.*, 15: 867-910, 2001.

Saura et al., "High-Yield Isolation of Murine Microglia by Mild Trypsinization," *Glia*, 44:183-189, 2003.

Ulukaya et al., "Fenretinide and its relation to cancer," *Cancer Treatment Reviews*, 25: 229-235, 1999.

Wong et al., "An Adverse Property of a Familial ALS-Linked SOD1 Mutation Causes Motor Neuron Disease Characterized by Vacuolar Degeneration of Mitochondria," *Neuron*, 14: 1105-1116, 1995.

Alam et al., "Conformationally Defined 6-*s-trans*-Retinoic Acid Analogs. 2. Selective Agonists for Nuclear Receptor Binding and Transcriptional Activity," *J Med Chem*, 38: 2302-2310, 1995.

Crochemore et al, "Long-term Dietary Administration of Valproic Acid Does Not Affect, While Retinoic Acid Decreases, the Lifespan of G93A Mice, a Model for Amyotrophic Lateral Sclerosis," *Muscle and Nerve*, 39: 548-552, 2009.

Extended European Search Report, European Patent Application No. 09711963.0, 7 pages (Mar. 7, 2011).

Germain et al., "International Union of Pharmacology, LXIII Retinoid X Receptors," *Pharmacological Reviews*, 58(4): 760-772, 2006.

Hope et al., Retinoids Inhibit Phospholipase $A_2$ in Human Synovial Fluid and Arachidonic Acid Release from Rat Peritoneal Macrophages, *Inflammation*, 14(5): 543-559, 1990.

Jokic et al., "Retinoid receptors in chronic degeneration of the spinal cord: observations in a rat model of amyotrophic lateral sclerosis," *Journal of Neurochemistry*, 103: 1821-1833, 2007.

Kizaki et al., "Effects of Novel Retinoid X Receptor-Selective Ligands on Myeloid Leukemic Differentiation and Proliferation in Vitro," *Blood*, 87(5): 1977-1984, 1996.

Phillis et al., "Cyclooxygenases, lipoxygenases, and epoxygenases in CNS: their role and involvement in neurological disorders," *Brain Research Reviews*, 52(2): 201-243, 2006.

Sheikh et al., "iV-(4-hydroxyphenyl)retinamide (4-HPR)-mediated biological actions involve retinoid receptor-independent pathways in human breast carcinoma," *Carcinogenesis*, 16(10): 2477-2486, 1995.

Vos et al., "Effects of Retinoid X Receptor-Selective Ligands on Proliferation of Prostate Cancer Cells," *The Prostate*, 32: 115-121, 1997.

Wang et al., "Molecular Cancer Therapeutics," *Mol Cancer Ther*, 5(4): 1060-1072, 2006.

* cited by examiner

A.

B.

A.

B.

A.

B.

A.

B.

C.

D.

A.

B.

A.

B.

C.

D.

SEQUENCE LISTING

<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
ccccagccct ccgacctaca a                                        21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
ccccggaagc aacccaaaca c                                        21

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
cagcacttca cccatcagtt                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ctggtcattg gaggcctttg                                          20

<210> SEQ ID NO 5
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 5
atgccgcccg gtgtcctt                                            18

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
tgggtccttg agcctcatca tca                                      23

<210> SEQ ID NO 7
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 7
ggtgcgcgtc ctgctctgta                                                   20

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
agtggcgtgt tcccgtgctc tcc                                               23

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
aggcgcctgg agaaaagtgg atgt                                              24

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gtggggctgg gagaggtgtg a                                                 21

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
cctgtgttcc accaggagat                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
aaggccaaac acagcatacc                                                   20

<210> SEQ ID NO 13
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 13
atgaaggtct ccaccactg                                                    19
```

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
gcattcagtt ccaggtca                                          18

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
aagtttgtca tgaatgattc cctc                                   24

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
gtctcactac ctgtgatgag t                                      21

<210> SEQ ID NO 17
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 17
atgagcacag aaagcatg                                          18

<210> SEQ ID NO 18
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 18
gaagactcct cccaggta                                          18

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ccttgggccg cgtctccttc                                        20

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

```
-continued

<400> SEQUENCE: 20
atggggtagg gacgctctcc tgag                                          24

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
catcagccct aatccatctg a                                             21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
cgcgactaac aatcaaagtg a                                             21

<210> SEQ ID NO 23
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 23
ctaggccaca gaattgaaag atct                                          24

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
gtaggtggaa attctagcat catcc                                         25
```

TREATMENT OF NEURAL DISEASES OR CONDITIONS

CROSS REFERENCE TO RELATED APPLICATIONS

This is the U.S. National Phase Application of PCT application No. PCT/CA2009/000208 filed on Feb. 20, 2009 and published in English under PCT Article 21(2) as International Publication No. WO 2009/103166. This application further claims the benefit, under 35 U.S.C. §119(e), of U.S. provisional application Ser. No. 61/030,354, filed on Feb. 21, 2008 All of the above applications are incorporated herein by reference in their entirety.

TECHNICAL FIELD

The present invention generally relates to treatment of neural diseases or conditions. More specifically, the present invention relates to treatment of neural injury or neurodegenerative diseases, such as spinal cord injury and ALS.

BACKGROUND ART

The clinical management of numerous neurological disorders has been frustrated by the progressive nature of degenerative, traumatic, or destructive neurological diseases and the limited efficacy and serious side-effects of available pharmacological agents. Conditions such as degeneration, injury or trauma to the nervous system have eluded most conventional pharmacological attempts to alleviate or cure the conditions.

Traumatic injury to the spinal cord, also called spinal cord injury (SCI) leads to functional impairments due to the death of neurons and glial cells and to the disruption of the axonal pathways. The primary insult, however, triggers a cascade of pathological events, known as secondary injury, which develops hours and days after the primary injury, resulting in further tissue damage and functional loss. The inflammatory response contributes strongly to secondary damage after SCI by releasing cytokines, free radicals, eicosanoids and proteases, among other molecules (Jones et al. (2005) *Curr Pharm Des* 11: 1223-1236).

Currently, only one therapeutic agent, methylprednisolone (MP), is considered standard therapy after traumatic SCI. MP is a synthetic glucocorticosteroid that has been subjected to several large-scale human clinical trials and showed minor clinical benefits when administered within 48 hours of SCI.

Amyotrophic lateral sclerosis (ALS), also referred to as Lou Gehrig's disease, is a progressive neurodegenerative disorder caused by degeneration of motor neurons, and is associated with inflammation and elevated levels of reactive oxygen species. It ultimately results in muscle paralysis and respiratory failure. No effective treatment has yet been found for ALS, although riluzole has been recently approved for the treatment of ALS. Riluzole delays the onset of ventilator-dependence or tracheostomy and the deterioration of muscle strength in some patients. However, it is associated with several side-effects.

Thus, there is a need for novel methods and products to prevent and/or treat neural diseases and conditions such as SCI and/or ALS.

The present description refers to a number of documents, the content of which is herein incorporated by reference in their entirety.

SUMMARY OF THE INVENTION

The present invention generally relates to treatment of neural diseases or conditions, based on the use of a retinoic acid derivative, such as fenretinide, and/or analogs, derivatives, prodrugs, precursors thereof, and/or salts thereof. More specifically, the present invention relates to treatment of neural injury or neurodegenerative diseases, based on the use of a retinoic acid derivative, such as fenretinide, and/or analogs, derivatives, prodrugs, precursors thereof, and/or salts thereof.

In a first aspect, the present invention provides a method for treating neural injury or a neurodegenerative disease in a subject, said method comprising administering to said subject an effective amount of a retinoic acid derivative.

In another aspect, the present invention provides a use of a retinoic acid derivative for treating neural injury or a neurodegenerative disease in a subject.

In another aspect, the present invention provides a use of a retinoic acid derivative for the preparation of a medicament for treating neural injury or a neurodegenerative disease in a subject.

In another aspect, the present invention provides a composition for treating neural injury or a neurodegenerative disease in a subject, said composition comprising (a) a retinoic acid derivative; and (b) a pharmaceutically acceptable carrier.

In another aspect, the present invention provides a composition for the preparation of a medicament for treating neural injury or a neurodegenerative disease in a subject, said composition comprising: (a) a retinoic acid derivative; and (b) a pharmaceutically acceptable carrier.

In another aspect, the present invention provides a retinoic acid derivative for treating neural injury or a neurodegenerative disease in a subject.

In another aspect, the present invention provides a retinoic acid derivative for the preparation of a medicament for treating neural injury or a neurodegenerative disease in a subject.

In another aspect, the present invention provides a package comprising: (1) a retinoic acid derivative; and (2) instructions for use of said retinoic acid derivative for the treatment of neural injury or a neurodegenerative disease in a subject.

In another aspect, the present invention provides a package comprising: (1) a composition comprising (a) (i) a retinoic acid derivative; and (b) a pharmaceutically acceptable carrier; and (2) instructions for use of said composition for the treatment of neural injury or a neurodegenerative disease in a subject.

In an embodiment, the above-mentioned retinoic acid derivative is (i) fenretinide; (ii) a functional derivative, analog, conjugate, prodrug or precursor of fenretinide; (iii) a pharmaceutically-acceptable salt of (i) or (ii); or (iv) any combination of (i) to (iii).

In a further embodiment, the above-mentioned retinoic acid derivative is (i) fenretinide; (ii) a pharmaceutically-acceptable salt of fenretinide; or (iii) any combination of (i) and (ii).

In an embodiment, the above-mentioned method comprises administering to said subject an effective amount of (i) fenretinide; (ii) a pharmaceutically-acceptable salt of fenretinide; or (iii) any combination of (i) and (ii).

In an embodiment the above-mentioned use comprises the use of (i) fenretinide; (ii) a pharmaceutically-acceptable salt of fenretinide; or (iii) any combination of (i) and (ii).

In an embodiment, the above-mentioned composition comprises: (a) (i) fenretinide; (ii) a pharmaceutically-acceptable salt of fenretinide; or (iii) any combination of (i) and (ii); and (b) a pharmaceutically acceptable carrier.

In an embodiment, the above-mentioned method or use further comprises treatment or inhibition of (or the preparation of a medicament for the treatment or inhibition of) a condition associated with said neural injury selected from (a) neural inflammation; (b) loss of neural cell or tissue; (c)

increased neural arachidonic acid (AA) levels; (d) decreased neural docosahexaenoic acid (DHA) levels; (e) neural oxidative stress; and (f) any combination of (a) to (e).

In an embodiment, the above-mentioned composition, package or retinoic acid derivative is further for treating or inhibiting a condition following said neural injury, wherein said condition is selected from (a) neural inflammation; (b) loss of neural cell or tissue; (c) increased neural arachidonic acid (AA) levels; (d) decreased neural docosahexaenoic acid (DHA) levels; (e) neural oxidative stress; and (f) any combination of (a) to (e).

In another embodiment, the above-mentioned method or use further comprises treatment or inhibition of (or the preparation of a medicament for the treatment or inhibition of) a condition associated with said neurodegenerative disease/disorder, wherein said condition is selected from (a) decreased motor function; (b) increased neural arachidonic acid (AA) levels; (c) decreased neural docosahexaenoic acid (DHA) levels; (d) neural oxidative stress; (e) decreased number of motor neurons; (f) increased neural glial activation; and (g) any combination of (a) to (f).

In another embodiment, the above-mentioned composition, package or retinoic acid derivative is further for treating or inhibiting a condition associated with said neurodegenerative disease/disorder, wherein said condition is selected from (a) decreased motor function; (b) increased neural arachidonic acid (AA) levels; (c) decreased neural docosahexaenoic acid (DHA) levels; (d) neural oxidative stress; (e) decreased number of motor neurons; (f) increased neural glial activation; and (g) any combination of (a) to (f).

In another embodiment, the above-mentioned neural injury is injury to the central nervous system (CNS). In a further embodiment, the above-mentioned injury to the CNS is spinal cord injury (SCI). In a further embodiment, the above-mentioned SCI is acute SCI.

In an embodiment, the above-mentioned method or use further comprises increasing innervation (or the preparation of a medicament for increasing innervation) following said neural injury.

In an embodiment, the above-mentioned composition, package or retinoic acid derivative is further for increasing innervation following said neural injury.

In an embodiment, the above-mentioned innervation is serotonergic innervation.

In another embodiment, the above-mentioned AA levels are phospholipid-bound AA levels.

In another embodiment, the above-mentioned DHA levels are phospholipid-bound DHA levels.

In another embodiment, the above-mentioned neurodegenerative disease is Amyotrophic Lateral Sclerosis (ALS).

In another embodiment, the above-mentioned subject is a mammal. In a further embodiment, the above-mentioned mammal is a human.

Other objects, advantages and features of the present invention will become more apparent upon reading of the following non-restrictive description of specific embodiments thereof, given by way of example only with reference to the accompanying drawings.

SEQUENCE LISTING

Figure 1:
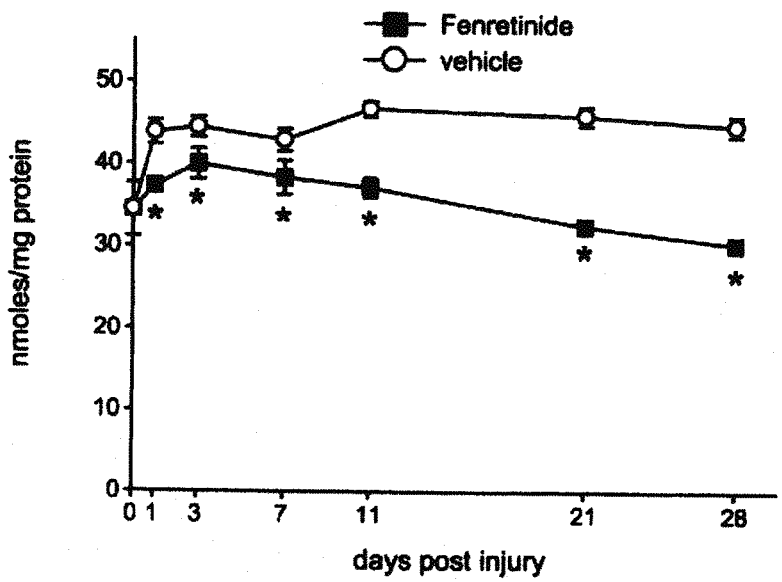
FIG. 1 shows the quantification of arachidonic acid (AA) and docosahexaenoic acid (DHA) levels in plasma and spinal cord tissue after SCI. (A) Treatment with fenretinide (black squares) led to a significant reduction in plasma AA levels compared to vehicle-treated mice (white circles) from day 1 to 28 after SCI. (B) DHA plasma levels were significantly higher from 3 to 28 dpi (days post-injury) in mice treated with fenretinide (black squares) as compared to control mice (white circles). (C, D). Treatment with fenretinide (black bar), but not with vehicle (white bar) also caused a significant decrease in AA (C) and an increase in DHA levels (D) in the spinal cord at day 3 post-SCI ($*p<0.05$; $**p<0.01$)
Figure 1:
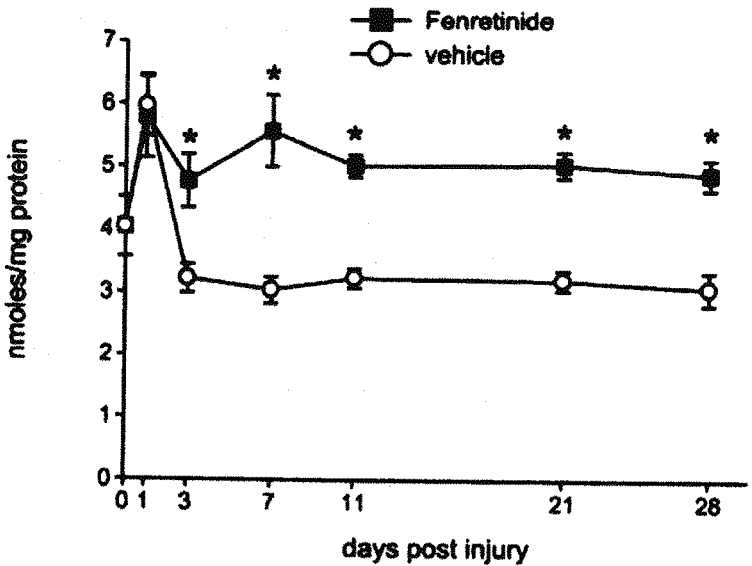
Figure 1:
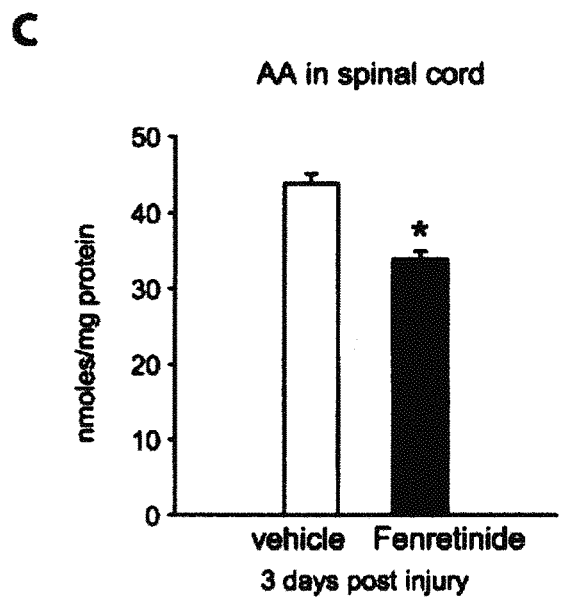
Figure 1:
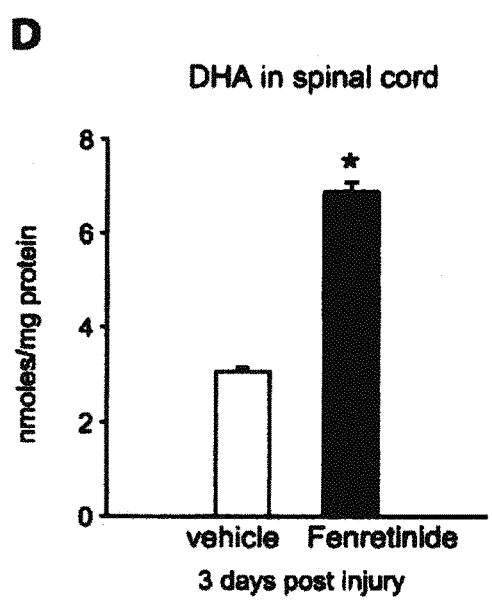

The Sequence Listing is submitted as an ASCII text file, created on Aug. 16, 2010, ~5 KB, which is incorporated by reference herein.

DISCLOSURE OF THE INVENTION

Described herein are studies using a mouse model of spinal cord injury (SCI) and a mouse model of ALS. The results described herein show that administration of fenretinide, a retinoic acid derivative, following SCI results in a significant enhancement in locomotor performance, tissue sparing, serotonergic fiber innervation, and motoneuron survival. Fenretinide treatment following SCI was also associated with (a) modulation of polyunsaturated fatty acid (PUFA) levels, and more particularly with decreased AA levels and increased DHA levels in both the plasma and the spinal cord; (b) reduction in the expression of pro-inflammatory mediators such as IL-1β, TNF-α, sPLA$_2$ GIIA and iNOS in the spinal cord; and (c) attenuation of the oxidative stress in the injured spinal cord. The data presented herein also show that administration of fenretinide to mutant SOD1 transgenic mice (ALS mouse model) results in (a) improve motor function, (b) prolonged survival, (c) improved ω-3:ω-6 poly unsaturated fatty acid (PUFA) ratios in the plasma and the CNS, (d) reduced lipid peroxidation/oxidative stress in the plasma and in the CNS, (e) increased number of motor neurons, and (f) decreased glial activation in the CNS.

Accordingly, in a first aspect, the present invention provides a method for treating neural injury or a neurodegenerative disease/disorder in a subject, said method comprising administering to said subject an effective amount of (i) a retinoic acid derivative; (ii) a functional analog, conjugate, prodrug or precursor of (i); (iii) a pharmaceutically-acceptable salt of (i) or (ii); or (iv) any combination of (i) to (iii). In an embodiment, the above-mentioned retinoic acid derivative increases, and/or induces the production of, ceramides.

In embodiments, retinoic acid derivatives which may be used in the present invention, include, for example:

(A) esters of all-trans-retinoic acid having the following formula:

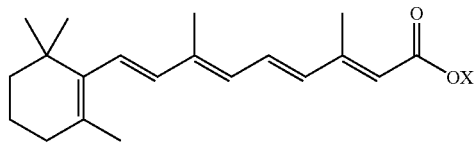

wherein X is selected from:

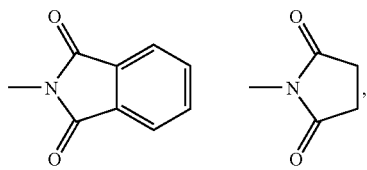

2-cyclohexylethyl; 10-carbomethoxydecyl; 4-hydroxybutyl; cholesteryl; mixed m- and p-vinylbenzyl; and 4-bromobenzyl;

(B) esters of all-trans-retinoic acid having the following formula:

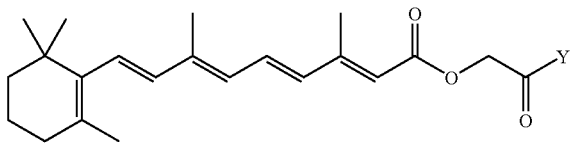

wherein Y is selected from cholesteryloxy; phenyl; 4-bromophenyl; 4-methoxyphenyl; 4-nitrophenyl; 4-hydroxyphenyl; 4-methylphenyl; 4-cyanophenyl; 4-ethoxyphenyl; 4-acetoxyphenyl; 2-naphthyl; 4-biphenyl; 2,5-dimethoxyphenyl; 2,4-dichlorophenyl; 2,4-dimethylphenyl; 3,4-diacetoxyphenyl; 3,4,5-trimethoxyphenyl; and 2,4,6-trimethylphenyl; and (C) amides of all-trans-retinoic acid having the following formula:

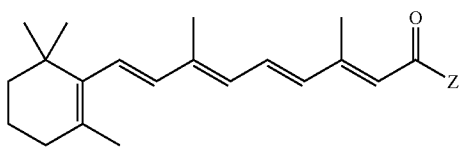

wherein Z is selected from: n-propylamino; tert-butylamino; 1,1,3,3-tetramethylbutylamino; 1-morpholino; 4-hydroxyphenylamino; 4-carbomethoxy-2-hydroxyphenylamino; beta-(3,4-dimethoxyphenyl)-ethylamino; 2-benzothiazolylamino; 1-imidazolyl; 1-(2-nicotinoylhydrazolyl); 1-benzotriazolyl; 1-(1,2,4-triazolyl),

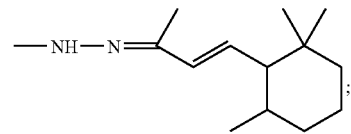

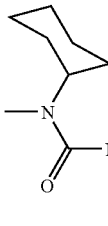

; and 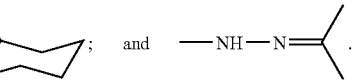

In another embodiment, the above-mentioned retinoic acid derivative is (i) fenretinide (all-trans-N-(4-hydroxyphenyl) retinamide); (ii) a functional derivative, analog, conjugate, prodrug or precursor of fenretinide; or (iii) a pharmaceutically-acceptable salt of (i) or (ii).

In another aspect, the present invention provides the use of a retinoic acid derivative for treating neural injury or a neurodegenerative disease/disorder, or for the preparation of a medicament for treating neural injury or a neurodegenerative disease/disorder, in a subject.

In another aspect, the present invention provides a composition comprising (a) a retinoic acid derivative; and (b) a pharmaceutically acceptable carrier, for treating neural injury or a neurodegenerative disease/disorder, or for the preparation of a medicament for treating neural injury or a neurodegenerative disease/disorder, in a subject.

In another aspect, the present invention provides a retinoic acid derivative for treating neural injury or a neurodegenerative disease/disorder, or for the preparation of a medicament for treating neural injury or a neurodegenerative disease/disorder, in a subject.

In an embodiment, the above-mentioned retinoic acid derivative (i) fenretinide; (ii) a functional derivative, analog, conjugate, prodrug or precursor of fenretinide; (iii) a pharmaceutically-acceptable salt of (i) or (ii); or (iv) any combination of (i) to (iii). In a further embodiment, the above-mentioned retinoic acid derivative is (i) fenretinide; (ii) a pharmaceutically-acceptable salt of fenretinide; or (iii) any combination of (i) and (ii).

In embodiments, the above-mentioned method results in or further comprises treatment or inhibition of a condition following said neural injury, wherein said condition is selected from (a) neural inflammation; (b) loss of neural cell or tissue (i.e., results in improved neuronal survival); (c) increased neural arachidonic acid (AA) levels; (d) decreased neural docosahexaenoic acid (DHA) levels; (e) neural oxidative stress; and (f) any combination of (a) to (e).

In embodiments, the above-mentioned use, retinoic acid derivative, and/or composition results in or is further for the treatment or inhibition of a condition following said neural injury, wherein said condition is selected from (a) neural inflammation; (b) loss of neural cell or tissue (i.e., results in improved neuronal survival); (c) increased neural arachidonic acid (AA) levels; (d) decreased neural docosahexaenoic acid (DHA) levels; (e) neural oxidative stress; and (f) any combination of (a) to (e).

In an embodiment, the above-mentioned treatment or inhibition of neural inflammation is associated with (i) decreased TNF-α levels; (ii) decreased IL-1β levels; (iii) decreased iNOS levels; (iv) decreased sPLA$_2$ GIIA levels, or (v) any combination of (i) to (iv).

In embodiments, the above-mentioned method, use, retinoic acid derivative, and/or composition further results in or is further for increasing innervation following said neural injury. In an embodiment, the innervation is serotonergic innervation.

In an embodiment, the above-mentioned method results in or further comprises treatment or inhibition of a condition associated with said neurodegenerative disease/disorder (e.g., ALS), wherein said condition is selected from (a) decreased motor function; (b) increased neural arachidonic acid (AA) levels; (c) decreased neural docosahexaenoic acid (DHA) levels; (d) neural oxidative stress; (e) decreased number of motor neurons; (f) increased neural glial activation (e.g., CNS inflammation); and (g) any combination of (a) to (f).

In an embodiment, the above-mentioned use, retinoic acid derivative, and/or composition results in or further comprises treatment or inhibition of a condition associated with said neurodegenerative disease/disorder (e.g., ALS), wherein said condition is selected from (a) decreased motor function; (b) increased neural arachidonic acid (AA) levels; (c) decreased neural docosahexaenoic acid (DHA) levels; (d) neural oxidative stress; (e) decreased number of motor neurons; (f) increased neural glial activation; and (g) any combination of (a) to (f).

In an embodiment, the above-mentioned neurodegenerative disease/disorder is ALS.

Fenretinide (all-trans-N-(4-hydroxyphenyl)retinamide), which has CAS registry number 65646-68-6, is a synthetic retinoid of the following formula:

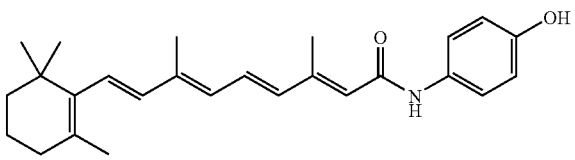 [SMILES: CC1=C(/C=C/C(C)=C/C=C/C(C)=C/C(=O)Nc2ccc(O)cc2)C(C)(C)CCC1]

Functional derivatives, analogs, prodrugs or metabolites of fenretinide which have the ability, as described herein, to prevent and/or treat a neural disease or condition may also be used in the present invention. As used herein, a "fenretinide derivative" or "fenretinide analog" refers to a compound whose chemical structure comprises a 4-hydroxy moiety and a retinamide. Examples of derivatives/analogs/metabolites of fenretinide that may be used include, but are not limited to, 4-oxo-N-(4-hydroxyphenyl)retinamide (4-oxo-4-HPR), N-(4-methoxyphenyl)retinamide (4-MPR),4-Hydroxybenzylretinone, C-glycoside and arylamide analogues of N-(4-hydroxyphenyl)retinamide-O-glucuronide, including but not limited to 4-(retinamido)phenyl-C-glucuronide, 4-(retinamido)phenyl-C-glucoside, 4-(retinamido)benzyl-C-xyloside; and retinoyl β-glucuronide analogues such as, for example, 1-(β-D-glucopyranosyl)retinamide, 1-(D-glucopyranosyluronosyl)retinamide and bexarotene, described in WO 07/136,636, U.S. Patent Application No. 2006/0264514, U.S. Pat. Nos. 5,516,792, 5,663,377, 5,599,953, 5,574,177, Anding et al. (2007) *Cancer Res.* 67: 6270-6277 and Bhatnagar et al. (1991) *Biochem. Pharmacol.* 41: 1471-7.

Fenretinide and/or a pharmaceutically acceptable salt thereof is particularly suitable for use in the present methods as it is reported to have fewer side-effects compared to naturally-occurring retinoids including vitamin A (Ulukaya and Wood (1999) *Cancer Treat Rev.* 25: 229-35). The safety profile for fenretinide is excellent, as minimal side effects have been noted in a variety of clinical trials using fenretinide on a prophylactic basis (Ulukaya and Wood (1999), supra). Clinical trials have shown that fenretinide does not induce generalized vascular damage in humans (Reynolds and Lemons (2001) *Hematol. Oncol. Clin. North Am.* 15: 867-910). Fenretinide has also been used to treat subjects (2-21 years of age) with neuroblastoma to define fenretinide pharmacokinetics and maximal tolerated dose in children, and to assess short- and mid-term toxicity in this age range (Garaventa, et al. (2003) *Clin. Cancer Res.* 9: 2032-2039).

Fenretinide has been extensively studied because of its chemo-protective and anti-tumor activities described when used on a variety of malignant cells, including non-small lung cancer, neuroblastoma, Kaposi's sarcoma, breast cancer and glioma (Charles et al. (2001) *Cancer Chemother. Pharmacol.* 47: 444-450; Garaventa et al. (2003) *Clin. Cancer Res.* 9: 2032-2039; Lippman et al. (2001) *J. Natl. Cancer Inst.* 93: 605-618; Ponthan et al. (2003) *Oncol. Rep.* 10: 1587-1592; Puduvalli et al. (1999) *Clin. Cancer Res.* 5: 2230-2235; Rao et al. (1998) *Breast Cancer Res. Treat.* 48: 265-271), and has been approved for clinical trials of cancer patients and is being evaluated in clinical chemoprevention trials in lung, breast, and bladder cancer (Costa et al. (1995) *Ann. NY Acad. Sci.* 768: 148-62). Fenretinide has also been granted Orphan Disease status both in US and Europe for the following indications (see http://www.cancertechnology.co.uk/): (1) Treatment of malignant bone disease (EU), granted Jan. 26, 2007, designation number EU/3/06/426; (2) Treatment of soft tissue sarcoma (EU), granted Jan. 30, 2007, designation number EU/3/06/427; (3) Treatment of Ewing's sarcoma family of tumors (US), granted Feb. 1, 2007, designation number 06-2361.

An "effective amount" of an agent (e.g., a retinoic acid derivative such as fenretinide, or an analog, derivative, prodrug or metabolite thereof, or a pharmaceutically-acceptable salt thereof) or composition as referred to herein is an amount which is capable of achieving a prophylactic and/or therapeutic effect on neural injury (e.g., spinal cord injury) or a neurodegenerative disease/disorder (e.g., ALS), of a neural cell and/or tissue (e.g., CNS tissue, e.g., spinal cord). A prophylactic and/or therapeutic effect includes, but is not limited to, reduction in apoptosis/destruction (i.e., loss of) of neural cells and/or tissue; increase survival of neural cells and/or tissue (e.g. neurons); reduction or delay of neurodegeneration, recovery of motor function; reduction in long-term damage to neural cells/tissue and/or to surrounding cells/tissue; decrease of the inflammation in neural cells/tissues (e.g., SCI-associated inflammation, SLA-associated inflammation); reduction in the oxidative stress in neural cells/tissues; decrease in neural AA levels (e.g., phospholipid-bound AA levels); increase in neural DHA levels (e.g., phospholipid-bound DHA levels); improvement in behavioral reflexes; and increased survival/survival time.

An effective amount or dose of any one active agent will vary somewhat from compound to compound, subject to subject, and will depend upon factors such as the condition of the subject, the target site of action, the patient's weight, the route of delivery, and other factors that will be recognized by those skilled in the art. Such dosages can be determined in accordance with routine pharmacological procedures known to those skilled in the art, particularly in light of the disclosure provided herein and current dosing practices of known active agents.

For example, fenretinide has been used systemically by achieving a plasma level of about 0.1, 2, 3, 5 µM to 10 or 20 µM. For oral dosing, fenretinide is typically used at 50 or 100 to 500 or 1000, 2000 or 3000 mg/m$^2$ body surface area per day. In particular embodiments, 0.1 to 10 µM plasma concentrations are achieved.

In an embodiment, the above-mentioned agent is administered/used as soon as the injury to CNS (e.g., during acute SCI) or the neurodegenerative disorder is diagnosed. In an embodiment, the treatment is continued until the inflammatory process resulting from, or associated with, the injury or disorder is resolved. In another embodiment, the above-mentioned administration or use is daily administration or use. In an embodiment, the above-mentioned administration or use is performed for a cycle of about 28 days. In another embodiment, the above-mentioned administration or use is performed for a cycle of about 5 days. In a further embodiment, the above-mentioned cycle is repeated several times (e.g., once, twice, three times, four times, five times, six times, seven times, etc.). In a further embodiment, the above-mentioned administration or use is interrupted between said cycles. In a further embodiment, the above-mentioned interruption is for about 3 days.

An agent (e.g., a retinoic acid derivative such as fenretinide, or an analog, derivative, prodrug or metabolite thereof, or a pharmaceutically-acceptable salt thereof) of the present invention for treatment of neural injury or a neurodegenerative disease/disorder can be prepared for therapeutic use in accordance with the methods disclosed herein by formulating the agents with a pharmaceutically acceptable carrier/excipient to obtain a composition (pharmaceutical composition or medicament). Accordingly, the present invention provides a composition comprising (a) a retinoic acid derivative; and (b) a pharmaceutically acceptable carrier, for treating neural injury or a neurodegenerative disease/disorder, or for the preparation of a medicament for treating neural injury or a neurodegenerative disease/disorder, in a subject. In an embodiment, the above-mentioned composition comprises:

(a) (i) fenretinide; (ii) a functional derivative, analog, conjugate, prodrug or precursor of fenretinide; (iii) a pharmaceutically-acceptable salt of (i) or (ii); or (iv) any combination of (i) to (iii); and (b) a pharmaceutically acceptable carrier.

In an embodiment, the above-mentioned composition comprises (i) fenretinide; (ii) a pharmaceutically-acceptable salt of fenretinide; or (iii) any combination of (i) and (ii).

In the manufacture of a pharmaceutical formulation, the active agent, including a physiologically acceptable salt thereof, is typically admixed with, inter alia, an acceptable carrier/excipient. The carrier is acceptable in the sense of being compatible with any other ingredients in the formulation and not be deleterious to the subject. The carrier can be a solid or a liquid, or both, and is preferably formulated with the compound as a unit-dose formulation, for example, a tablet, which can contain from 0.5% to 95% by weight of the active agent. One or more active agents can be incorporated in the formulations of the invention, which can be prepared by any of the well-known techniques of pharmacy consisting essentially of admixing the components, optionally including one or more accessory ingredients. See, e.g., Remington: The Science and Practice of Pharmacy, Alfonso R. Gennaro, editor, 20$^{th}$ ed. Lippincott Williams & Wilkins: Philadelphia, Pa., 2000.

The formulations of the invention include those suitable for oral, buccal (e.g., sub-lingual), parenteral (e.g., subcutaneous intramuscular, intradermal, or intravenous), topical (i.e., mucosal surfaces and airway surfaces), and neural administration, although the most suitable route in any given case will depend on the nature and severity of the condition being treated and on the nature of the particular active agent which is being used.

Formulations comprising fenretinide are described, for example, in WO 02/05869, WO 07/115,134, WO 04/069203, U.S. Patent publication No. 2005/0106216, U.S. Pat. Nos. 4,874,795, and 5,972,911.

In an embodiment, an agent of the invention (e.g., a retinoic acid derivative such as fenretinide, or a derivative, analog, prodrug or metabolite thereof, or a pharmaceutically-acceptable salt thereof) is administered such that it comes into contact with neural cells or neural tissue, such as central nervous system (CNS) cells or tissue. Such tissue includes brain and spinal cord (e.g., cervical, thoracic, or lumbar) tissue. As such, in embodiments a compound of the invention can be administered to treat neural cells/tissue in vivo via direct intracranial injection or injection into the cerebrospinal fluid. Alternatively, the compound can be administered systemically (e.g. intravenously) and may come into contact with the affected neural tissue via lesions (where the blood-brain barrier is compromised), or, in a further embodiment, may be in a form capable of crossing the blood-brain barrier and entering the neural system (e.g., CNS). Further, in an embodiment, a composition of the invention may be formulated for such administration to neural tissue.

Formulations suitable for oral administration can be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations can be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet can be prepared by compressing or molding a powder or granule containing the active agent, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent (s). Molded tablets can be made by molding, in a suitable machine, the powdered compound moistened with an inert liquid binder.

Formulations suitable for buccal (sub-lingual) administration include lozenges having the active agent in a flavored base, usually sucrose and acacia or tragacanth; and pastilles containing the active agent in an inert base such as gelatin and glycerin or sucrose and acacia.

Formulations for parenteral administration are conveniently sterile aqueous preparations of the active agent, which preparations are preferably isotonic with the blood of the intended recipient. These preparations can be administered by means of subcutaneous, intravenous, intramuscular, or intradermal injection. Such preparations can conveniently be prepared by admixing the compound with water or a glycine buffer and rendering the resulting solution sterile and isotonic with the blood. Formulations for parenteral administration can also be mixed, for example, with vitamin E and/or other suitable food antioxidants and food supplements [such as Peptamen® (Nestlé)].

Formulations suitable for topical application (e.g., in the oral passage, nasopharynx, or oropharynx) take the form of an ointment, cream, lotion, paste, gel, spray, aerosol, or oil. Carriers which can be used include vaseline, lanoline, polyethylene glycols, alcohols, transdermal enhancers, and combinations of two or more thereof.

In an embodiment, the above-mentioned treatment comprises the use/administration of more than one (i.e., a combination of) active/therapeutic agent (e.g., a retinoic acid derivative such as fenretinide, or a derivative, analog, prodrug or metabolite thereof, or a pharmaceutically-acceptable salt thereof). The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time.

It is also contemplated that the active compounds/compositions/formulations of the instant invention (or combinations thereof) may be used alone or in combination with other therapeutics currently used to prevent and/or treat neural diseases and/or conditions (e.g., spinal cord injury or neurodegenerative diseases/disorders) or their associated effects (e.g., pain). For example, the compounds/compositions/formulations of the instant invention may be used in combination with (i.e., administered before, after, or simultaneously with) methylpredisolone, pain relievers or pain killers, or neurotrophic factors.

The invention further provides kits or packages (e.g., commercial packages) comprising the above-mentioned composition(s) or agent(s) together with instructions for their use for the treatment of neural injury or a neurodegenerative disease/disorder in a subject. Accordingly, in another aspect, the present invention provides a kit or package comprising:

(i) a retinoic acid derivative, such as fenretinide, and/or analogs, derivatives, prodrugs, precursors thereof, and/or salts thereof, or the above-mentioned composition; and (ii) instructions for its use for the treatment of neural injury or a neurodegenerative disease/disorder in a subject.

Such kit may also comprise, for example, containers, devices for administering the agent/composition, etc.

In an embodiment, the above-mentioned neural injury is an injury to the CNS. In a further embodiment, the above-mentioned injury to the CNS is spinal cord injury (SCI). In a further embodiment, the above-mentioned SCI is acute SCI. In another embodiment, the above-mentioned neurodegenerative disease/disorder is ALS. In a further embodiment, the above-mentioned ALS is familial ALS.

Neural injury and neurodegenerative disease/disorders generally refers to diseases or conditions resulting in, or associated with, damage to neural cells/tissue. Such damages may be the result, for example, of a physical trauma to neural tissue and/or of inflammation/oxidative stress within a neural tissue. Reference to spinal cord injury (SCI) herein includes any form of physical, chemical or genetic trauma to the spinal cord. A physical trauma includes a tissue insult such as an abrasion, incision, contusion, puncture, compression etc., such as can arise from traumatic contact of a foreign object with any locus of or appurtenant/adjacent to the head, neck or vertebral column. Other forms of traumatic injury can arise from constriction or compression of CNS tissue by an inappropriate accumulation of fluid (for example, a blockade or dysfunction of normal cerebrospinal fluid or vitreous humor fluid production, turnover, or volume regulation, or a subdural or intracranial hematoma or edema). Similarly, traumatic constriction or compression can arise from the presence of a mass of abnormal tissue, such as a metastatic or primary tumor or from disease (poliomyelitis, spina bifida, Friedreich's Ataxia, etc.). In an embodiment, the method, use, composition and/or package of the present invention are useful for the prevention and/or treatment of secondary injury resulting from an initial insult/injury to the CNS (e.g., spinal cord).

As used herein, the terms "subject" or "patient" are used interchangeably are used to mean any animal, preferably a mammal, including humans, non-human primates as well as domestic and farm animals, and zoo, sports or pet animals such as dogs, horses, cats, cows etc. In an embodiment, the subject is a human.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The articles "a," "an" and "the" are used herein to refer to one or to more than one (i.e., to at least one) of the grammatical object of the article. The following examples are illustrative of various aspects of the invention, and do not limit the broad aspects of the invention as disclosed herein.

EXAMPLES

The present invention is illustrated in further detail by the following non-limiting examples.

Example 1

Materials and Methods

Spinal cord contusion and drug administration. All surgical procedures were approved by the McGill University Animal Care Committee and followed the guidelines of the Canadian Council on Animal Care. Adult (8-10 weeks old) female BALB/c mice (Charles River Canada) were anaesthetized with ketamine:xylazine:acepromazine (50:5:1 mg/kg). After performing a laminectomy at the $11^{th}$ thoracic vertebrae, the exposed spinal cord was contused using the Infinite™ Horizons Impactor device (Precision Scientific Instrumentation, Lexington, Ky.). Moderate injuries were made using a force of 50 kDynes and tissue displacements ranging between 400-600 µm (Ghasemlou et al. (2005) *Exp. Neurol.* 196: 9-17).

Fenretinide preparation and treatment. Fenretinide powder was resuspended in 95% ethanol under sterile conditions to generate a 2 µg/µL stock solution. This solution was incorporated into a daily liquid diet of Peptamen™ (Nestle Canada, Brampton, ON) at a dose of 5 mg/kg/day for oral consumption as described previously (Guilbault et al. (2008) *Am J Respir Cell Mol Biol* 38: 47-56). The suspension was protected from light and kept at 4° C. before treatment of the mice. One hour following surgery and for the subsequent three days, fenretinide was administered by gavage in two doses, each suspended in 300 μL of Peptamen™. Gavage was chosen as the method of drug delivery immediately after surgery due to the loss of appetite and reduced food intake during the first 48 h after injury. After day three, mice were fed the fenretinide/Peptamen™ mixture. At this point mice were separated into individual cages in order to ascertain the amount of food and drug consumed. Following day 3, the diet was administered every morning with careful monitoring of the quantity consumed by each mouse. More specifically, the daily fenretinide dose was incorporated into 12 ml of Peptamen™, which represents 80% of the daily mouse food consumption, to ensure 100% consumption. The food was given to the mice in the mid-morning. The diet for control animals was prepared and administered in the same fashion as the drug treatment; however, control animals received Peptamen™ with no fenretinide added but with an equivalent amount of ethanol.

Lipid analysis. (A) For SCI studies: in order to establish plasma kinetics, blood samples were taken from the saphenous vein at day 0, 1, 3, 7, 11, and 21 post-injury. On day 28, blood samples were obtained by intra-cardiac puncture. All blood samples were mixed with 10 μl of EDTA to prevent coagulation and centrifuged at 350×g for 7 minutes at 4° C. The plasma was then removed and lipids were extracted with chloroform-methanol (2:1 vol/vol) containing 1 mM butylated hydroxyanisole (BHA), as previously described (Folch et al. (1957) *J Biol Chem* 226: 497-509). The lipid fractions were dried under nitrogen and resuspended in heptane as previously described (De Sanctis (1991) *Med Sci Res* 19: 335-337). Phospholipids were identified by thin layer chromatography extraction. Diazomethane was used to esterify the released fatty acids and the esters were identified by GC/MS (Hewlett Packard 5880A, WCOT) capillary column (Supelco™-10, 35 m×0.5 mm, 1 μm thick) using commercial standards (Sigma-Aldrich, Oakville, ON, Canada). Total levels of DHA and AA as well as phospholipid-bound DHA, phospholipid-bound AA, malonyldialdehyde (MDA) and nitrotyrosine were assessed in both plasma and spinal cord samples. (B) For ALS studies: Plasma, spinal cord, cerbral cortex and brainstem samples were all analyzed to determine the lipid concentration of each. Ceramide, phospholipid-bound docosahexaenoic acid (DHA), phospholipid-bound arachidonic acid (AA), malonyldialdehyde (MDA) and nitrotyrosine levels were assessed in all samples. To determine the lipid concentration of tissue and plasma samples, analysis was performed using an enzyme-linked immunosorbent assay (ELISA) method. The extracted lipid fractions were dried under nitrogen and resuspended in heptane. Separation of phospholipids was performed by thin-layer chromatography (TLC), detected by iodine. The separated lipid samples were then subjected to ELISA to ascertain the concentrations of each lipid species. The phospholipids from the dry silica, once resuspended in ethanol, were used to coat Nunc™ plates specific for lipid binding. The plates were then washed and incubated with blocking buffer for 1 hr at 37° C. (PBS, 0.1% Tween™ 20, and 1% bovine serum albumin). Following the blocking step, the plates were incubated with murine IgM (Sigma-Aldrich) antibody (Ab) specific for the particular lipid species desired for 1 hr at 37° C. Following another wash, the plates were incubated with anti-mouse IgM Ab conjugated with peroxidase for 1 hr at 37° C. The final step involved incubating the plates with the peroxidase substrate (TMB; Roche, Laval, QC). The intensity of the colorimetric reaction was determined by spectrophotometry at 405 nm and the level of each lipid species was calculated using a standard curve as a reference. Outliers were identified as data falling outside ±2 standard deviations from the group mean when the point in question was removed.

RT-PCR. A 5 mm length of the spinal cord containing the lesion site was harvested at 1 dpi from experimental and control groups. The three spinal cords were pooled and RNA was extracted using RNeasy™ Lipid Tissue kit (Qiagen, Mississauga, Ontario, Canada). PCR amplification was performed with specific primers for mouse IL-1β, TNF-α, MCP-1, COX-1, COX-2, iNOS, cPLA$_2$ GIVA, iPLA$_2$ GVIA and sPLA$_2$ GIIA (Table I). Peptidylprolyl isomerase A (PPIA) was used as a control to normalize the cDNA samples used for PCR amplification. Changes in mRNA expression between vehicle- and fenretinide-treated samples were quantified as a ratio of the PPIA optical density value using ImageQuant™ 5.0 software.

TABLE I

Primers used for PCR amplification

| Gene | Primer sequence (5' - 3') | | SEQ ID NO: |
|---|---|---|---|
| COX-1 | Forward: | CCCCAGCCCTCCGACCTACAA | 1 |
| | Reverse: | CCCCGGAAGCAACCCAAACAC | 2 |
| COX-2 | Forward: | CAGCACTTCACCCATCAGTT | 3 |
| | Reverse: | CTGGTCATTGGAGGCCTTTG | 4 |
| cPLA$_2$ GIVA | Forward: | ATGCCGCCCGGTGTCCTT | 5 |
| | Reverse: | TGGGTCCTTGAGCCTCATCATCA | 6 |
| iPLA$_2$ GVIA | Forward: | GGTGCGCGTCCTGCTCTGTA | 7 |
| | Reverse: | AGTGGCGTGTTCCCGTGCTCTCC | 8 |
| sPLA$_2$ GIIA | Forward: | AGGCGCCTGGAGAAAAGTGGATGT | 9 |
| | Reverse: | GTGGGGCTGGGAGAGGTGTGA | 10 |
| iNOS | Forward: | CCTGTGTTCCACCAGGAGAT | 11 |
| | Reverse: | AAGGCCAAACACAGCATACC | 12 |
| MCP1 | Forward: | ATGAAGGTCTCCACCACTG | 13 |
| | Reverse: | GCATTCAGTTCCAGGTCA | 14 |
| IL-1β | Forward: | AAGTTTGTCATGAATGATTCCCTC | 15 |
| | Reverse: | GTCTCACTACCTGTGATGAGT | 16 |
| TNFα | Forward: | ATGAGCACAGAAAGCATG | 17 |
| | Reverse: | GAAGACTCCTCCCAGGTA | 18 |
| PPIA | Forward: | CCTTGGGCCGCGTCTCCTTC | 19 |
| | Reverse: | ATGGGGTAGGGACGCTCTCCTGAG | 20 |

Functional assessment. Locomotor recovery was evaluated in an open-field test using the Basso Mouse Scale (BMS) (Basso et al. (2006) *J Neurotrauma* 23: 635-659), which was specifically developed for locomotor testing after contusion injuries in mice. The BMS analysis of hindlimb movements and coordination was carried out by two independent trained assessors, and the consensus score taken. The final score is presented as mean±SEM. The BMS is a compressed scale with a maximum score of 9 as compared to the 20-point BBB scale for rats. Therefore small differences in the BMS can account for larger functional differences.

Histological analysis. (A) For spinal cord injury studies: 28 days post-lesion, mice were perfused with 4% paraformaldehyde in 0.1M phosphate buffer (PB). 5 mm length of the spinal cord containing the lesion site was removed, cryoprotected with 30% sucrose in 0.1M PB, and cut in serial sections (16 μm thick). Serial tissue sections were immunostained using rat polyclonal antibodies against glial fibrillary acidic protein (GFAP) (1/400; Zymed Labs) and rabbit polyclonal antibodies against 5-hydroxytryptamine (5-HT) (1/5000; Sigma, Aldrich). In addition, one series of serial sections of the spinal cord were stained with cresyl violet to quantify neuronal loss. Tissue sections were viewed with an Axioskop™ 2 Plus microscope (Zeiss) and images captured using a QImaging Retiga™ 1300 camera, and quantification done using BioQuantn™ Nova Prime image analysis system (BioQuant Image Analysis Corp.). Tissue sparing was calculated by delineating the GFAP stained areas, and neuronal survival was assessed by counting the neuron profiles in the ventral horn below the level of the central canal of the spinal cord in tissue sections stained with cresyl violet. Assessment of serotonergic fiber innervation was performed by calculating the area occupied by serotonergic axons in the ventral horns of spinal cord sections taken at a distance of 1000 μm caudal to the lesion site.

(B) For ALS studies: Mice were deeply anaesthetized with a cocktail of ketamine (7.5 mg/ml) and xylazine (0.5 mg/ml) administered via intraperitoneal injection at a dose of 20 ml/kg of body weight. Animals were then sacrificed by transcardial perfusion with 4% paraformaldehyde in 0.1 M phosphate buffered saline (PBS). The fourth lumbar spinal cord segment, identified by its contribution to the sciatic nerve was carefully removed, post-fixed for 1 hour in 4% paraformaldehyde solution and cryoprotected overnight in 30% sucrose in 0.1 M PBS. 10 μm serial sections were cut on a Leica™ cryostat (Leica Microsystems GmbH, Wetzlar, Germany) and immunostained with rat polyclonal antibodies against GFAP (1:400; Zymed Labs) or rat polyclonal antibodies against Mac-2 (1:4) to detect the presence and activation of glia. Digital images of both ventral horns were captured every 300 μm. Images were imported into SigmaScan™ Pro Image Measurement Software Version 5.0.0 (SPSS Inc., Chicago, Ill.) and activated astrocytes and microglia were quantified by exceeding an intensity threshold. Values were then normalized for the total area examined. Serial sections from a separate set were stained for Nissle body detection using cresyl violet staining and the number of motor neurons surviving in the ventral horn were quantified. Outliers were identified as data falling outside ±2 standard deviations from the group mean when the point in question was removed.

In vitro microglia activation. Mouse microglial cultures were prepared as described previously (Saura J et al., 2003. Glia 44:183-189). Briefly, confluent mixed glial cultures prepared from the neonatal cerebral cortex were treated for 30 min with trypsin (0.08%) in the presence of 0.25 mM EDTA and 0.5 mM $Ca^{2+}$. This treatment results in the detachment of an intact layer of cells containing virtually all the astrocytes and leaves a population of firmly attached cells identified as >98% microglia as assessed by counts of CD11b-immunoreactive cells (Saura J et al., (2003) Glia 44:183-189). These microglial cells were stimulated by adding lipopolysaccharides (LPS) (10 ng/ml) in DMEM/F12 with 1% penicillin/streptomycin and 1% vitamins for 6 h. The determination of the LPS concentration and incubation time was based on earlier experiments used to optimize conditions for measuring TNFα release from activated microglia. Treatment with fenretinide (0.625 or 1.25 μM in DMEM/F12) was initiated 18 hours prior to LPS stimulation, and continued together with LPS stimulation. The protocol for fenretinide treatment was based on previous studies on toxicity and reduction of TNFα levels in macrophages. The amount of TNFα released in 50 μl of the conditioned medium was determined by ELISA.

Transgenic mice. $SOD1^{G93A}$ [B6SJL-Tg(SOD1*G93A) 1Gur/J] transgenic mice, available at Jackson Laboratories (Stock No. 002726) were utilized. These animals were derived from a colony maintained on a C57BL/6 background. All animals were housed and bred at the McGill University Health Centre Research Institute Animal Facility. Mice were maintained in cages with sterile wood-chip bedding and kept in ventilated racks. All animal housing, breeding and experimentation were performed under specific pathogen-free conditions in a barrier facility. Pups were genotyped between 21 and 28 days of age using real-time quantitative polymerase chain reaction (qPCR) in accordance with the Jackson Laboratory protocols. Mutant SOD1 transgenic animals selected for experimentation were separated (1 animal/cage) for the duration of all studies. Mice were supplied with NIH-31—modified irradiated mouse diet (Harlan Teklad, Indianapolis, Ind.) ad libitum at all times. Beginning at day 30, mice used for experimentation were also given 12.5 mL of liquid diet (Peptamen™ liquid diet; Nestle Canada, Brampton, ON, Canada) 5 days per week containing either 5 mg/kg of fenretinide or an equivalent volume of vehicle (95% ethanol). After randomly assigning mice to either the fenretinide or control (vehicle) group, each mouse was then assigned randomly to one of three experimental groups to analyze behavior, plasma lipid concentration or histology. All procedures performed followed Canadian Council of Animal Care guidelines.

Tissue collection for fatty acid analysis. Mice were euthanized by inhaling $CO_2$ followed by cardiac puncture exsanguination. Blood collected was processed as described in the next section. The lumbar spinal cord segments, identified using the ribs and vertebrae as a guide, were transected and all spinal cord tissue was removed and homogenized before storing in 1 mM butylated hydroxy anisole (BHA) in chloroform/methanol (2:1 vol) at −80° C. until analysis was performed to maintain sample integrity. Cerebral cortex and brainstem samples were collected, homogenized and stored separately in the same BHA solution. Blood samples collected were treated under the same protocol as the samples extracted at different time points.

Blood collection. Blood samples were collected at day 60, 90 and 120 in addition to the time at the clinical endpoint mentioned above. Mice were placed under a heating lamp for 5 minutes before sampling. Mice were then placed in a holding device and one hind limb was immobilized and shaved. The saphenous vein was pierced with a 25 G needle and 100 μL of blood was collected and mixed with 10 μL of 0.5M EDTA to prevent coagulation. Samples were then centrifuged at 350×g for 7 minutes at 4° C. and 40 μl of plasma was removed and stored in 400 μl of the BHA solution described above. All samples were stored at −80° C. until analysis was performed.

Motor function analysis. Motor function was assessed by Rota-rod (Med Associates Inc., St. Albans, Vt.) two times per week beginning at 70 days of age. An acclimatization period of 3 days was implemented before beginning measurements to allow animals to become familiar with the apparatus. Animals were placed on the rod with a constant rotation of 16 rpm and the time latency to fall was used as a measurement of motor function. Animals remaining on the apparatus after 300 seconds were given a perfect score and the trial was ended. Three consecutive trials were performed with a one minute rest period between each trial and the best result of the three trials was recorded. Mice used for plasma analysis were also included in the Rota-rod experiments as it was determined after evaluating their performance that it was not impaired. In the rare event that an animal's performance improved, the lower "pre-improvement" time point was dropped as it was not considered representative of their true ability given the progressive nature of paralysis in SOD1$^{G93A}$ mice.

Survival. SOD1$^{G93A}$ mice typically develop the first signs of motor impairment around 90 days of age. The initial stages present with a resting tremor and slight gait impairment which progress to complete hind limb paralysis at the end stage. The clinical end point was determined to occur when a mouse was unable to right itself in less than 30 seconds after being turned on its side or when greater than 20% weight loss had occurred.

Analysis of mouse genotype by real-time RT-QPCR. Amplification of DNA obtained from tail tissue was performed on the Stratagene™ MX-4000 sequence detector (Stratagene, La Jolla, Calif.). PCR was performed using the SYBR Green Quantitative™ RT-PCR kit (Sigma, St. Louis, Mo.). The amplification program for SOD1$^{G93A}$ DNA consisted of an enzyme activation step for 3 min at 95° C., followed by 40 cycles of a denaturing step for 30 s at 95° C., an annealing step for 30 s at 60° C. and an extension step for 45 s at 72° C. A melting-curve analysis was performed after amplification to determine specificity of the PCR products (which were also confirmed with gel electrophoresis). Two sets of primers were used, in separate reaction flasks, to amplify both the WT and transgenic SOD1 genes: Tg forward: 5'-CAT CAG CCC TAA TCC ATC TGA-3' (SEQ ID NO: 21), Tg reverse: 5'-CGC GAC TAA CAA TCA AAG TGA-3' (SEQ ID NO: 22), WT forward: 5'-CTA GGC CAC AGA ATT GAA AGA TCT-3' (SEQ ID NO: 23), and WT reverse: 5'-GTA GGT GGA AAT TCT AGC ATC ATC C-3' (SEQ ID NO: 24). Both primer sets were diluted to a final concentration of 250 nM and tested to optimize conditions.

Statistical analyses. (A) For SCI studies: Data are presented as mean±standard error of measurement (SEM). Statistical analyses were performed using a t-test or two-way repeated measures ANOVA with post-hoc Tukey's test for multiple comparisons. Differences were considered significant at p<0.05. (B) For ALS studies: Data was analyzed and statistics were calculated with GraphPad Prism™ Version 4.03 software (GraphPad Software, San Diego, Calif.). Analysis of Rota-rod performance was performed by two-way analysis of variance (ANOVA) with Bonferroni post-tests at each time point. Survival was analyzed by log rank test of Kaplan-Meier cumulative survival plots and an un-paired, non-parametric t-test of mean survival time. Comparisons of lipid concentrations across the duration of the study were also analyzed by two-way ANOVA with Bonferroni post-tests while comparisons at day 120 were made with unpaired, non-parametric t-tests. Motor neuron, microglia and astrocyte comparisons were also made with non-parametric t-test analysis. Significance for all analyses was set at a two-tailed p value of ≤0.05. Data are displayed as mean±SEM.

Example 2

Fenretinide Modulates AA and DHA Levels after SCI

The plasma levels of arachidonic acid (AA), a pro-inflammatory fatty acid, rapidly increased as early as 1 day after SCI from 35 nmoles/mg protein to 45 nmoles/mg protein (p<0.05). The levels remained plateaued at the elevated level until day 28 (p<0.001; FIG. 1A). In contrast, the plasma levels of docosahexaenoic acid (DHA), an anti-inflammatory and protective fatty acid, is transiently increased at day 1 after SCI and then sharply decreased at day 4 post-injury and then maintained at this low level for the 28 day duration of the study (p<0.01, see figure FIG. 1B). Treatment with fenretinide resulted in a statistically significant difference in the plasma levels of AA starting at day 1 post-injury and continuing to decrease even further throughout the duration of the study. Surprisingly, this was accompanied by a concomitant increase in DHA levels in the plasma to above naïve control levels for the either duration of the study.

It was then assessed whether fenretinide could also modulate the AA and DHA levels in the injured spinal cord at 3 dpi, the first time point at which AA and DHA levels were significantly modulated in plasma. A similar decrease in AA (p<0.05) and increase in DHA (p<0.001; FIG. 1C, D) was detected in injured spinal cord tissue.

Example 3

Fenretinide Enhances Functional Recovery After SCI

Figure 2:
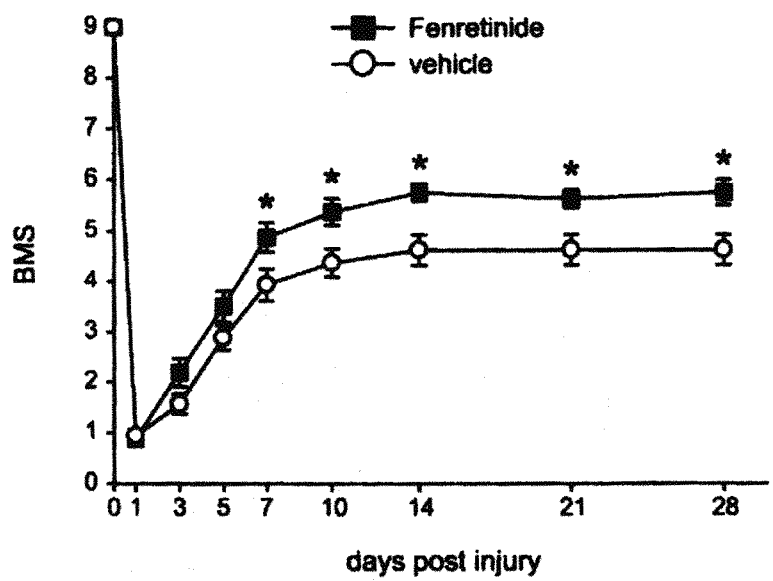
FIG. 2 shows (A) a time course of locomotor recovery evaluated using the Basso Mouse Scale (BMS) and (B) locomotor BMS subscores. Note that animals treated with fenretinide (black squares) show significantly enhanced motor skills starting from day 7 after SCI in the BMS and in the subscores ($*p<0.05$) as compared to their vehicle-treated counterparts (white circles)
Figure 2:
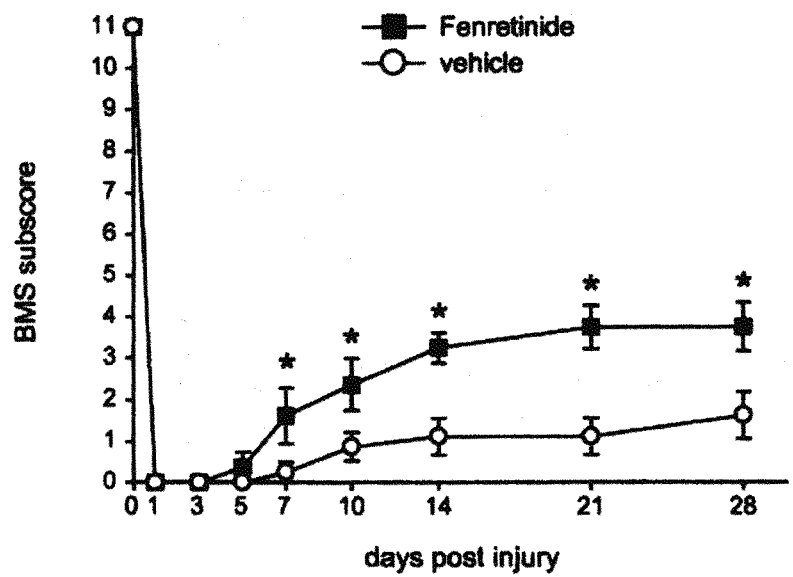

The effect of fenretinide on enhancement of functional recovery and tissue protection after SCI was evaluated. The results presented in FIG. 2A show that daily administration of fenretinide started 1 hour after SCI improved locomotor function assessed using the 9-point Basso Mouse Scale (BMS) as compared with the vehicle-treated mice (FIG. 2A; *p<0.05; Two Way RM-ANOVA, Tukey post-hoc test). Post-hoc analysis revealed significant differences in BMS score starting at day 7 dpi and remaining significantly enhanced during the duration of the follow up. At 28 dpi, vehicle-treated mice were able to step occasionally or frequently but without coordination (score 4.6). In contrast, mice treated with fenretinide displayed plantar stepping with occasional coordination and more parallel paw position (score 5.8). In addition, fine locomotor skills assessed by the BMS subscores also showed a significant improvement in mice treated with fenretinide from day 7 to 28 after SCI. At 28 dpi, mice given with fenretinide had a mean subscore 2.2 points higher than vehicle-treated mice (FIG. 2B).

Example 4

Fenretinide Reduces/Prevents Tissue Damage After SCI

Figure 3:
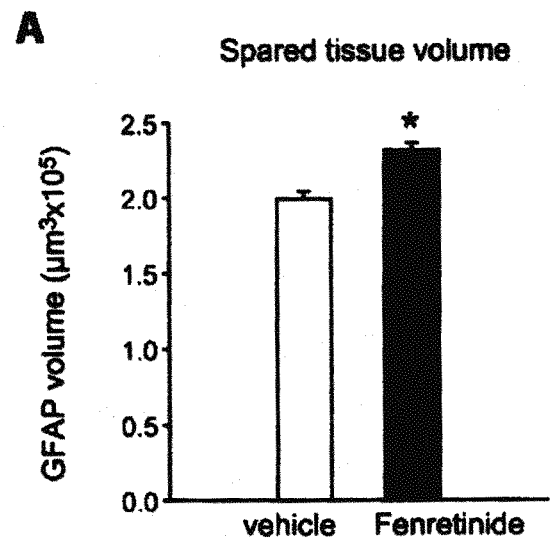
FIG. 3 shows quantification of tissue sparing assessed by staining for Glial fibrillary acidic protein (GFAP) at 28 days after SCI. (A) Mice treated with fenretinide (black bar) displayed a significant reduction in tissue loss as compared to control mice (white bar). (B) Tissue sparing was significantly improved at the epicenter and in adjacent/surrounding areas in mice treated with fenretinide (black squares) as compared to mice treated with vehicle only (white circles). (C) Mice treated with fenretinide (black bars) also showed greater neuron survival in regions ranging from 300 to 500 µm rostral and caudal to the lesion epicentre, as compared to vehicle-treated mice (white bars). (D) Animals treated with fenretinide (black bar) display significantly greater serotonergic innervation in the ventral horns 1000 µm caudal to the lesion epicentre as compared to animal administered with the vehicle (white bar) ($*p<0.01$; $**p<0.001$)
Figure 3:
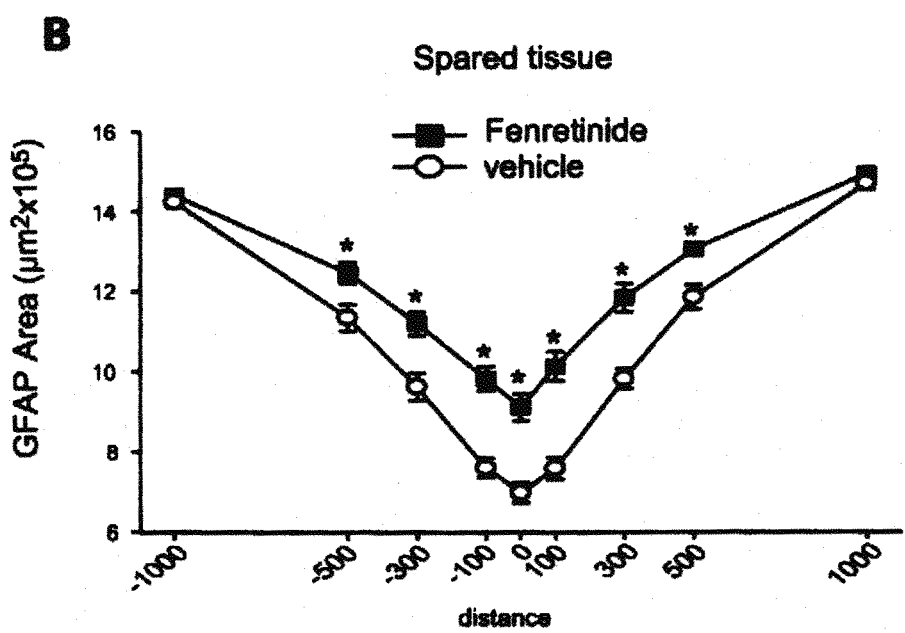
Figure 3:
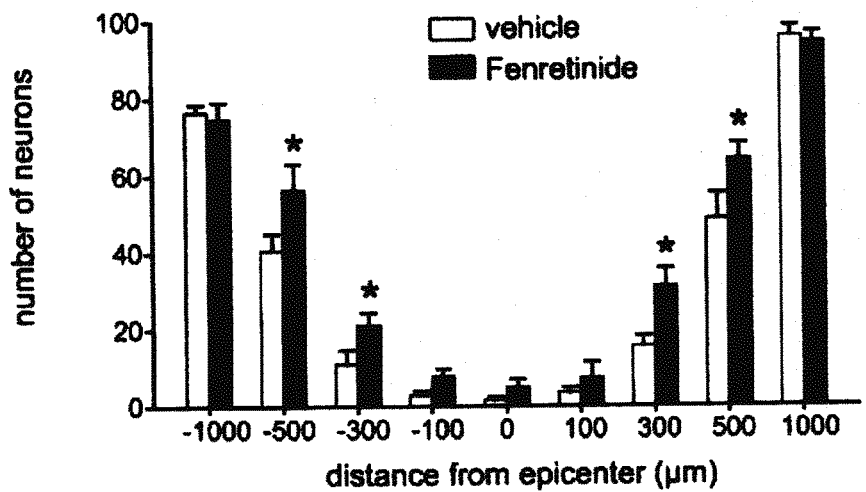
Figure 3:
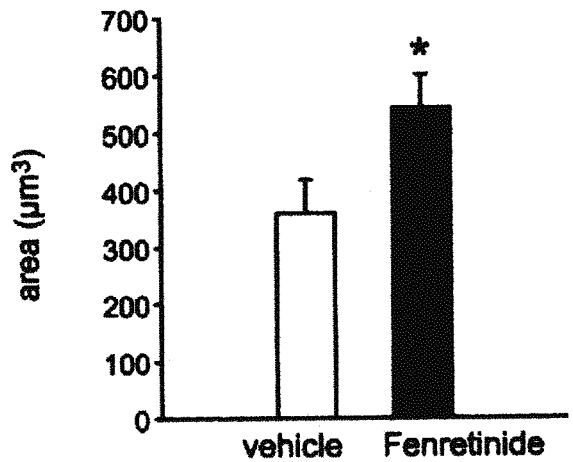

It was next assessed whether improvements in motor function mediated by fenretinide were associated with a reduction in spinal cord tissue damage. Histological sections of spinal cord stained for GFAP showed that fenretinide treatment reduced tissue loss by about 20% (FIG. 3A, **p<0.001, t-test). Prevention of tissue loss achieved after fenretinide treatment was evident at the lesion epicenter and in adjacent areas, for a distance of 1000 μm (FIG. 3B; *p<0.01; **p<0.001, Two-way RM-ANOVA, Tukey post hoc).

The effect of fenretinide on neuronal loss in the ventral horns after SCI was also evaluated. Spinal cord sections stained with cresyl violet displayed significantly greater numbers neurons in mice treated with fenretinide as compared to vehicle-treated mice, extending from 500 μm on either side of the lesion epicenter as compared to vehicle-treated lesioned control mice (FIG. 3C; *p<0.05, Two-way RM-ANOVA, Tukey post hoc test).

Since serotonergic axons play an important role in locomotion in rodents (Ribotta et al. (2000) *J Neurosci* 20: 5144-5152), the effect of fenretinide treatment on serotonergic fiber innervation caudal to the site of the injury was tested. Spinal cord sections stained for serotonin showed that fenretinide treatment resulted in ~60% greater serotonergic innervation in the ventral horn 1 mm caudal to the lesion epicenter (FIG. 3B, *p<0.01, t-test).

Example 5

Figure 4:
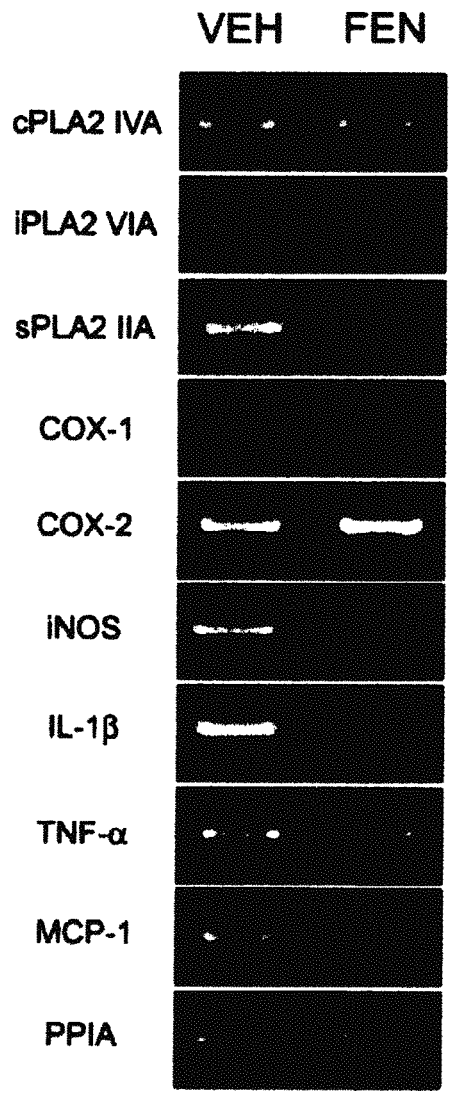
FIG. 4 shows quantification of mRNA encoding inflammatory-associated molecules in spinal cord samples following spinal cord injury. (A) Mice treated with fenretinide (FEN, right column) showed a marked reduction in the expression of mRNA encoding secreted phospholipase $A_2$ ($sPLA_2$) GIIA, inducible nitric oxide synthase (iNOS), interleukin-1β (IL-1β) and tumor necrosis factor-α (TNF-α) as compared to vehicle-treated mice (VEH, left column). (B, C) Spinal cords from mice treated with fenretinide (black bars) showed a significant reduction in the levels of malonyldialdehyde (MDA) (B) and nitrotyrosine (C) at 3 dpi ($*p<0.01$) as compared to their vehicle-treated counterparts (white bars)
Figure 4:
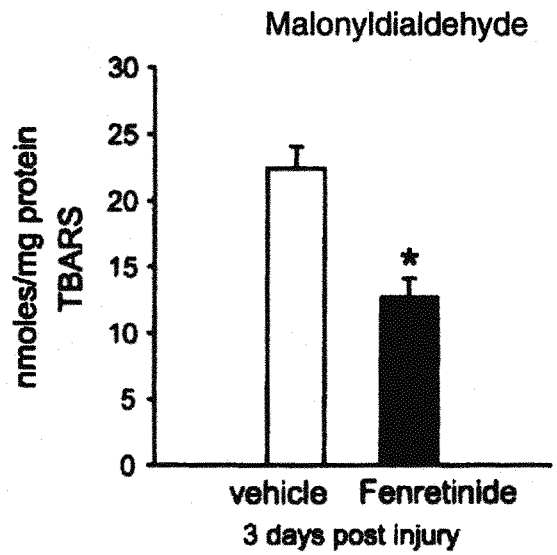
Figure 4:
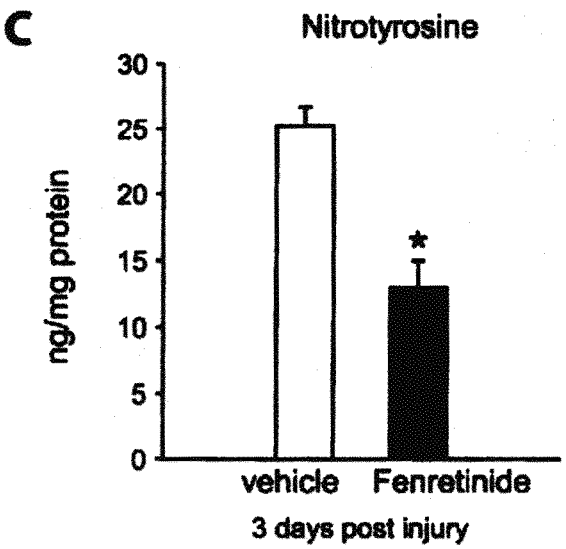

Fenretinide Reduces the Expression of Pro-inflammatory Mediators and Attenuates Oxidative Stress After SCI To test whether ferentidine modulates the inflammatory response, the mRNA levels of several pro-inflammatory mediators was measured by RT-PCR. The results showed that at 1 dpi, mRNA levels for TNF-α and IL-1β, two potent pro-inflammatory cytokines, were reduced by about 30% and 40%, respectively, after treatment with fenretinide (FIG. 4A). In addition, a 2-fold decrease in the mRNA levels of iNOS, an enzyme related to inflammation and oxidative stress, was observed following fenretinide treatment. Also, sPLA$_2$ GIIA mRNA levels, but not cPLA$_2$ GIVA and iPLA$_2$ GVIA mRNA levels, were reduced by about 50% after fenretinide treatment (FIG. 4A). No changes in COX-1, COX-2 and MCP-1 mRNA levels were observed (FIG. 4A).

The effect of fenretinide treatment on oxidative stress after SCI was assessed by measuring the levels of malonyldialdehyde (MDA), a product of lipid peroxidation, and nitrotyrosine, an indicator of damage induced by nitric oxide (NO). ELISA results from samples harvested at 3 dpi, a time point at which DHA levels in the spinal were significantly increased after injury, showed that levels of MDA and nitrotyrosine were decreased by about 2-fold in mice treated with fenretinide as compared to untreated control mice (FIG. 4B, C).

Example 6

Effect of Fenretinide on Microglial Cell Activation

Figure 5:
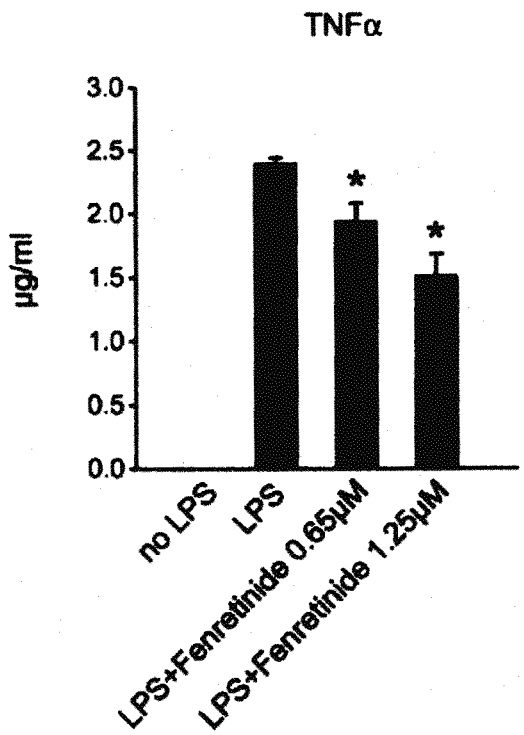
FIG. 5 shows the effects of fenretinide treatment (0.65 and 1.25 µM) on TNF-α release from microglial cell cultures stimulated with LPS (10 ng/ml). Fenretinide induced a significant reduction in TNF-α release from activated microglia ($*p<0.05$)
Figure 6:
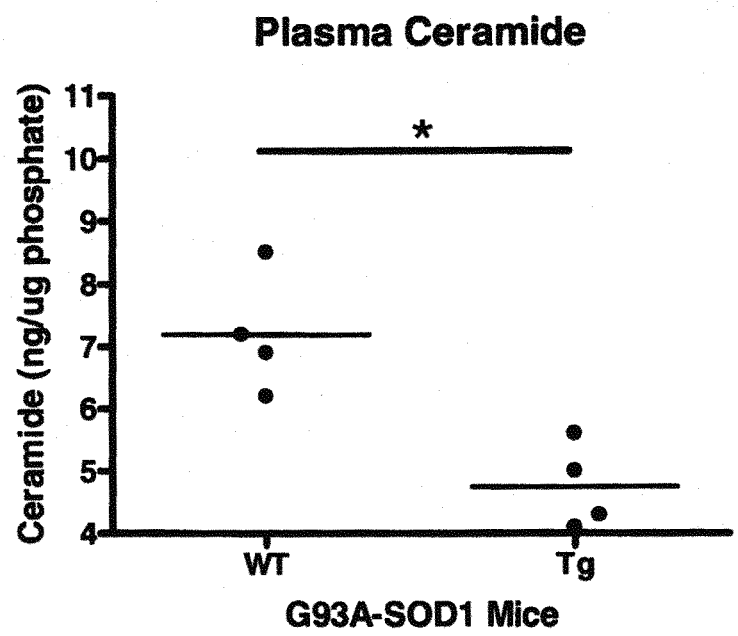
FIG. 6 shows plasma Phospholipid-bound ceramide levels in wild-type (WT) and $SOD1^{G93A}$ transgenic (Tg) mice. Each group was composed of n=4 animals and statistical significance was achieved with p=0.006.
Figure 7:
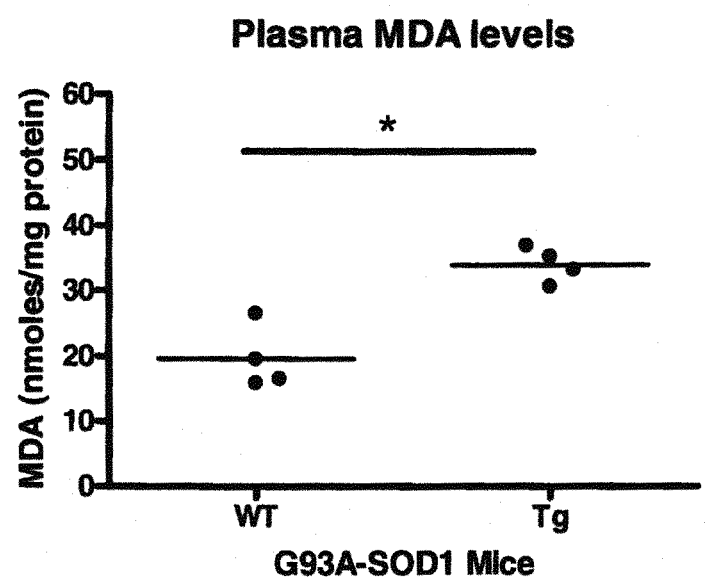
FIG. 7 shows plasma malonyldialdehyde (MDA) levels in wild-type (WT) and $SOD1^{G93A}$ transgenic (Tg) mice. Each group was composed of n=4 animals and statistical significance was achieved with p=0.002.
Figure 8:
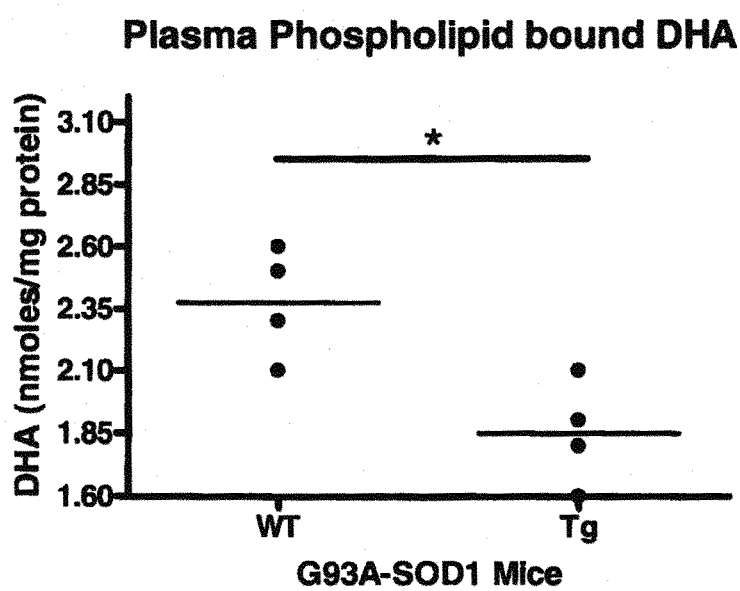
FIG. 8 shows plasma Phospholipid-bound docosahexaenoic acid (DHA) levels in wild-type (WT) and $SOD1^{G93A}$ transgenic (Tg) mice. Each group was composed of n=4 animals and statistical significance was achieved with p=0.01.
Figure 9:
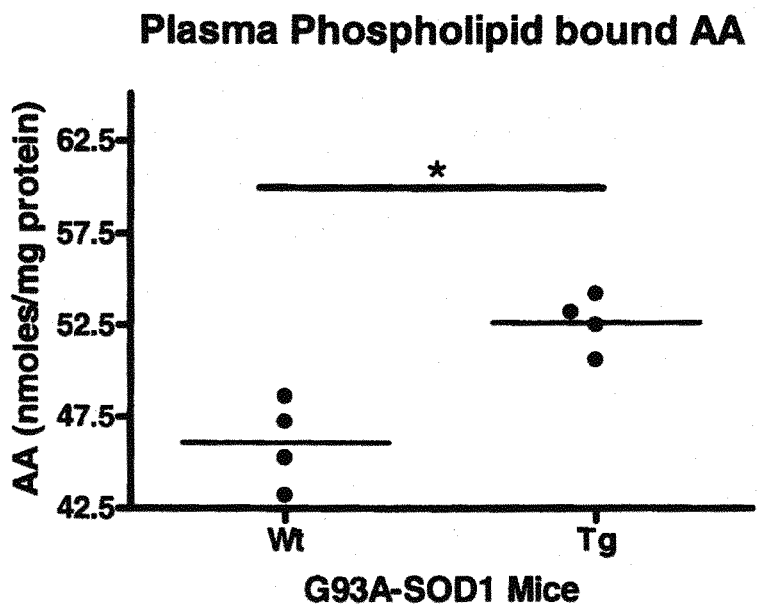
FIG. 9 shows plasma Phospholipid-bound arachidonic acid (AA) levels in wild-type (WT) and $SOD1^{G93A}$ transgenic (Tg) mice. Each group was composed of n=4 animals and statistical significance was achieved with p=0.003.
Figure 10:
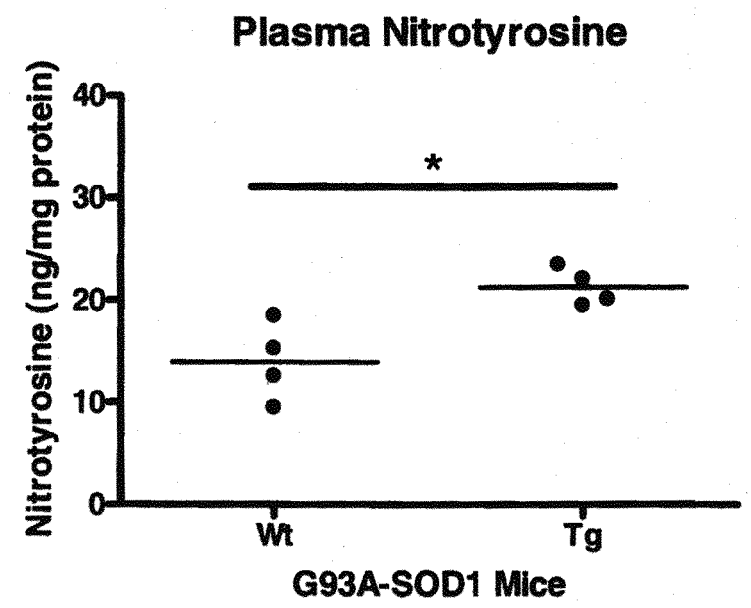
FIG. 10 shows plasma nitrotyrosine levels in wild-type (WT) and SOD1$^{G93A}$ transgenic (Tg) mice. Each group was composed of n=4 animals and statistical significance was achieved with p=0.01.
Figure 11:
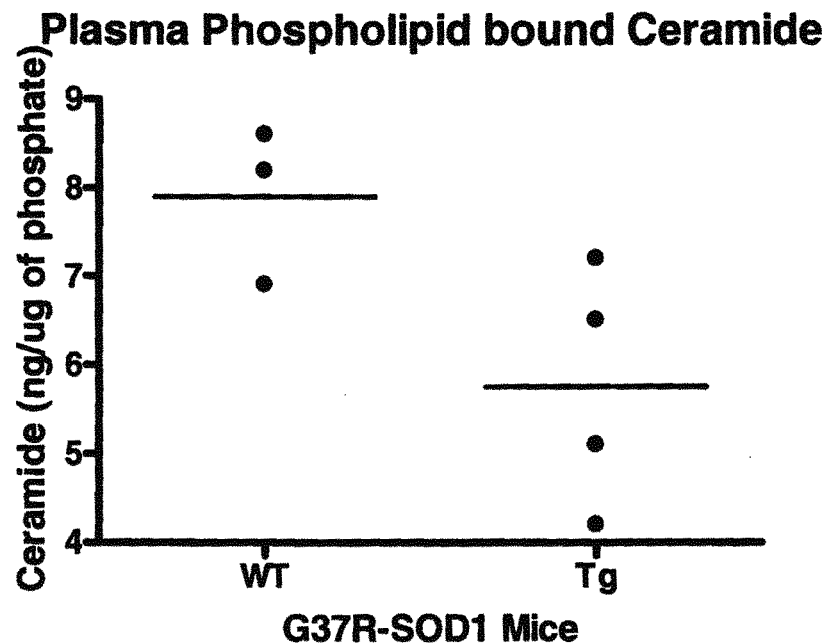
FIG. 11 shows plasma Phospholipid-bound ceramide levels in wild-type (WT) and SOD1$^{G37R}$ transgenic (Tg) mice. The wild type group was composed of 3 animals while the group of transgenic mice included 4 mice.
Figure 12:
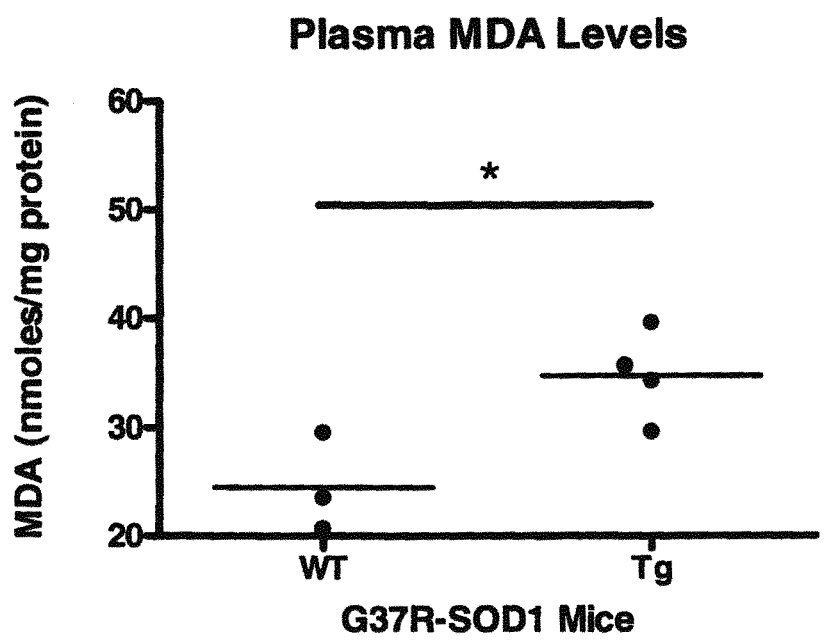
FIG. 12 shows plasma malonyldialdehyde (MDA) levels in wild-type (WT) and SOD1$^{G37R}$ transgenic (Tg) mice. The wild type group was composed of 3 animals while the group of transgenic mice included 4 mice. Statistical significance was achieved with p=0.02.
Figure 13:
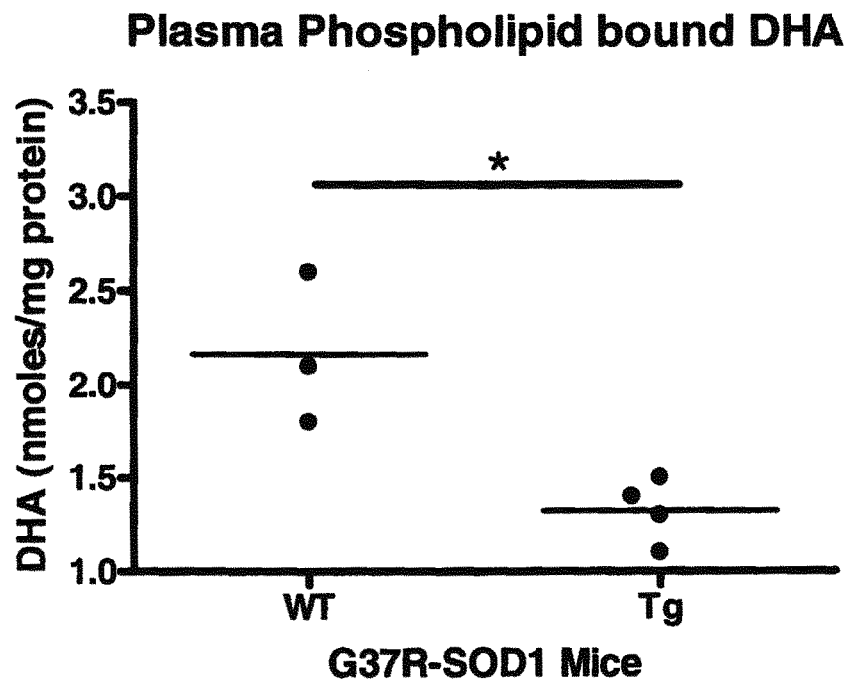
FIG. 13 shows plasma phospholipid-bound docosahexaenoic acid (DHA) levels in wild-type (WT) and SOD1$^{G37R}$ transgenic (Tg) mice. The wild-type group was composed of 3 animals while the group of transgenic mice included 4 mice. Statistical significance was achieved with p=0.01.
Figure 14:
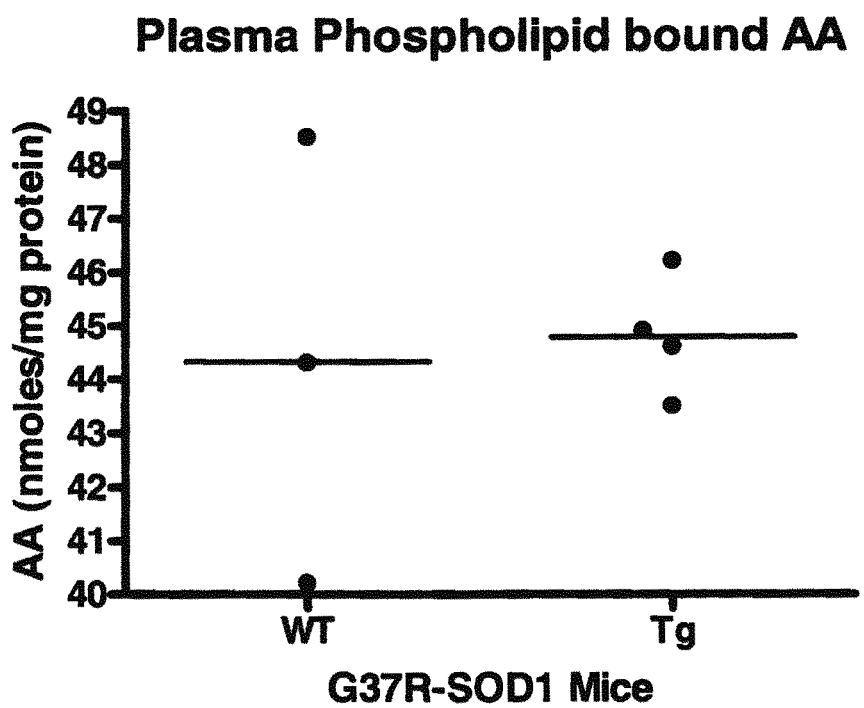
FIG. 14 shows plasma Phospholipid-bound arachidonic acid (AA) levels in wild-type (WT) and SOD1$^{G37R}$ transgenic (Tg) mice. The wild-type group was composed of 3 animals while the group of transgenic mice included 4 mice.
Figure 15:
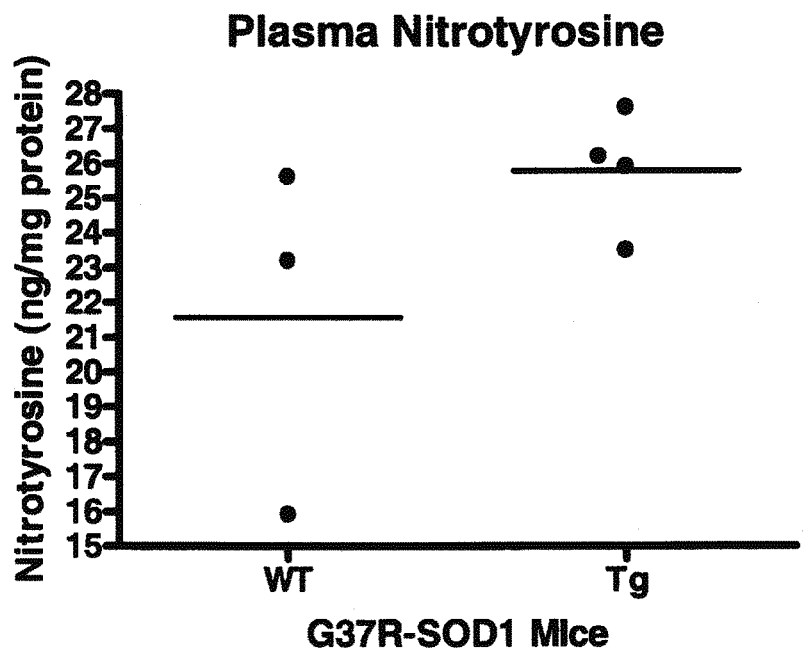
FIG. 15 shows plasma nitrotyrosine levels in wild-type (WT) and SOD1$^{G37R}$ transgenic (Tg) mice. The wild-type group was composed of 3 animals while the group of transgenic mice included 4 mice.

Fenretinide reduced pro-inflammatory mediator expression after SCI, suggesting that the drug modulates the inflammatory response. The effect of fenretinide on microglial cells was then studied. Microglial cells were activated in vitro by the addition of LPS (10 ng/ml) and the release of TNFα in the culture supernatant was measured. ELISA results from the supernatants obtained from microglial cells stimulated with LPS showed a 20% and 40% reduction in the protein levels of TNFα when treated with 0.625 and 1.25 µM of fenretinide, respectively (FIG. 5), as compared to untreated cells. These doses of fenretinide did not have any toxic effects on the cells based on cell viability and cell de-attachment studies. These results provide direct evidence that fenretinide reduces microglial activation. Similar results were obtained on activated bone marrow-derived macrophages.

Example 7

Plasma Levels of Molecules Associated with Inflammation and/or Oxidative Stress in ALS Mouse Models FIGS. 6-15 show a comparison of the plasma levels of various molecules generally associated with inflammation and/or oxidative damages/stress (ceramides, AA, DHA, MDA and nitrotyrosine) in wild-type mice vs. two mouse models of ALS, namely SOD1$^{G93A}$ (FIGS. 6-10) and SOD1$^{G37R}$ (FIGS. 11-15) transgenic mice. These mice, which over-express mutant forms of human Cu, Zn-superoxide dismutase (SOD1), show staged and age-dependent motor neuron degeneration with profound cellular and biochemical damage to nerve fibers and spinal cord tissue (Wong et al., 1995. *Neuron* 14: 1105-16; Hensley et al., 2006. *Antioxid redox signal* 8: 2075-87). The results presented in FIGS. 6-15 show that the levels of these molecules tend to be increased/higher in ALS mice as compared to normal mice.

Example 8

Effects of Fenretinide on Motor Function in SOD1$^{G93A}$ Transgenic Mice

Figure 16:
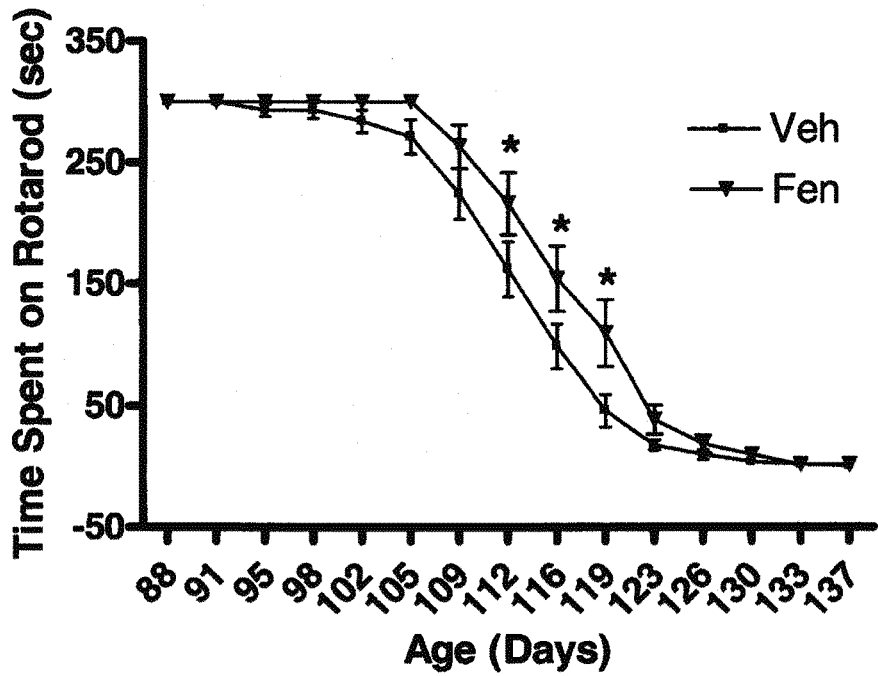
FIG. 16 shows the effects of fenretinide on Rota-rod performance. The effect of fenretinide treatment on motor performance in SOD1$^{G93A}$ transgenic mice from 88 to 137 days of age. Mice treated with 5 mg/kg fenretinide (Fen, inverted triangles) exhibited significantly improved motor performance compared to vehicle-treated controls (Veh, squares) by two-way ANOVA (p<0.0001). This test was followed by Bonferroni post-tests which additionally revealed significant improvements in the fenretinide-treated group at day 112, 116 and 119. Values are mean±SEM. * signifies p≤0.05. n≈20 for each group.

Impairment of motor function was measured by twice-weekly Rota-rod testing. SOD1$^{G93A}$ transgenic mice treated with fenretinide performed significantly better on the Rota-rod than sham-treated control animals suggesting that the disease phenotype can be modulated by fenretinide treatment. Sham-treated animals showed a decline in motor function 2 weeks before any impairment was detected in the fenretinide-treated group, indicating that treatment with fenretinide delays disease onset in this model. At all time points after day 91, the fenretinide-treated group performed better than control animals and this difference was significant ($p \leq 0.05$) independently at day 112, 116, and 119, as shown in FIG. 16. Performance at day 112 was increased from 162±23 sec (n=26) for vehicle-treated animals to 216±25 sec (n=19) in animals treated with 5 mg/kg fenretinide. Performance at day 116 was improved from 98±18 sec (n=26) for vehicle-treated animals to 154±27 sec (n=20) observed in fenretinide-treated animals. On day 119, fenretinide treatment enhanced performance from 46±13 (n=25) in vehicle-treated animals to 109±27 (n=18) in fenretinide-treated animals as shown in FIG. 16. In addition to these specific time points at which performance was significantly improved by fenretinide, overall Rota-rod performance across the entire duration of the study was found to be significantly enhanced in fenretinide-treated animals compared to control animals ($p \leq 0.0001$), depicted in FIG. 16.

Example 9

Effects of Fenretinide on Survival of SOD1$^{G93A}$ Transgenic Mice

Figure 17:
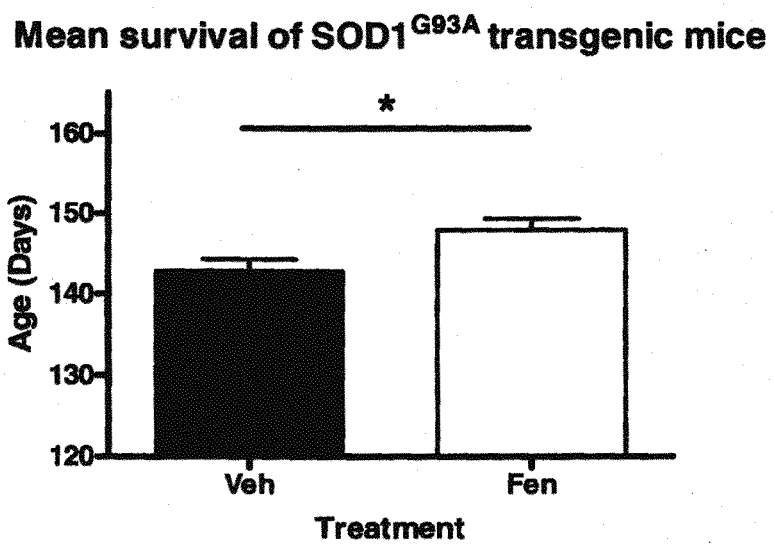
FIG. 17 shows the effect of fenretinide treatment on survival in SOD1$^{G93A}$ transgenic mice. (A) This figure depicts the mean survival of fenretinide (Fen) and vehicle-treated control (Veh) mice. The mean survival of mice treated with 5 mg/kg fenretinide was significantly improved from 142.9±1.3 d to 147.9±1.4 d compared to controls (p≤0.02) by non parametric t-test. Values are mean±SEM. * signifies p≤0.05. (B) This figure depicts the cumulative (Cum.) probability of survival for mice beginning treatment at 30 d of age with vehicle (Veh, squares) or 5 mg/kg fenretinide (Fen, inverted triangles). There is a significant increase in survival in treated SOD1$^{G93A}$ mice (p≤0.05). Median survival values are 148.5 days for fenretinide and 143.5 days for vehicle-treated mice. n=18 for Veh, n=12 for fen.
Figure 17:
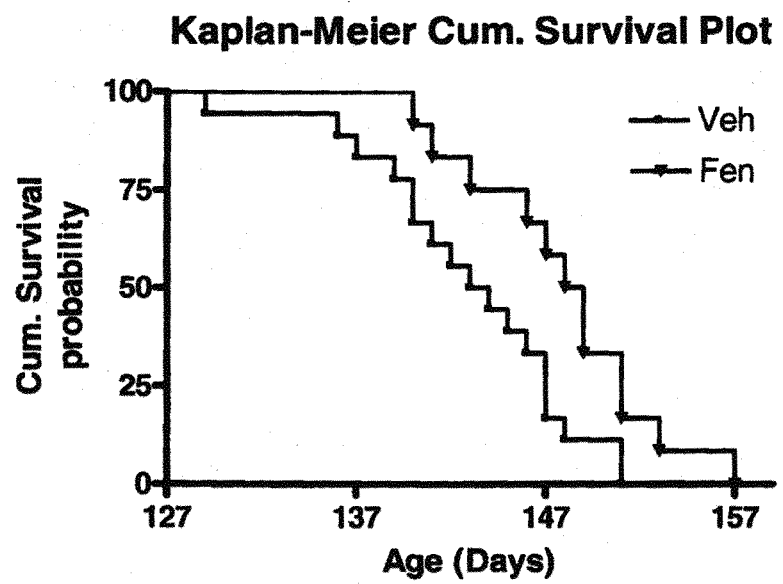

To establish whether fenretinide could enhance survival of SOD1$^{G93A}$ mice, the day at which animals reached the objective clinical endpoint was recorded as their duration of survival. Kaplan-Meier curves were used to calculate survival differences as well as a comparison of mean survival between drug-treated and control groups. The mean survival of SOD1$^{G93A}$ mice treated with fenretinide was significantly improved from 143±1.4 d (n=17) for control animals to 148±1.4 d (n=12) for drug-treated animals ($p \leq 0.05$), as shown in FIG. 17A. This difference constitutes an increase in survival of almost 10% from the onset of disease. The median survival of treated animals was also significantly ($p \leq 0.05$) higher than untreated, as evidenced from the Kaplan-Meier cumulative survival plot shown in FIG. 17B. Early mortality was also more common in control animals. More than 22% of sham-treated mice died before a single mouse treated with fenretinide reached the clinical endpoint, and 17% of fenretinide-treated animals remained alive after all control mice had reached the endpoint, as depicted in FIG. 17B.

Example 10

Figure 18:
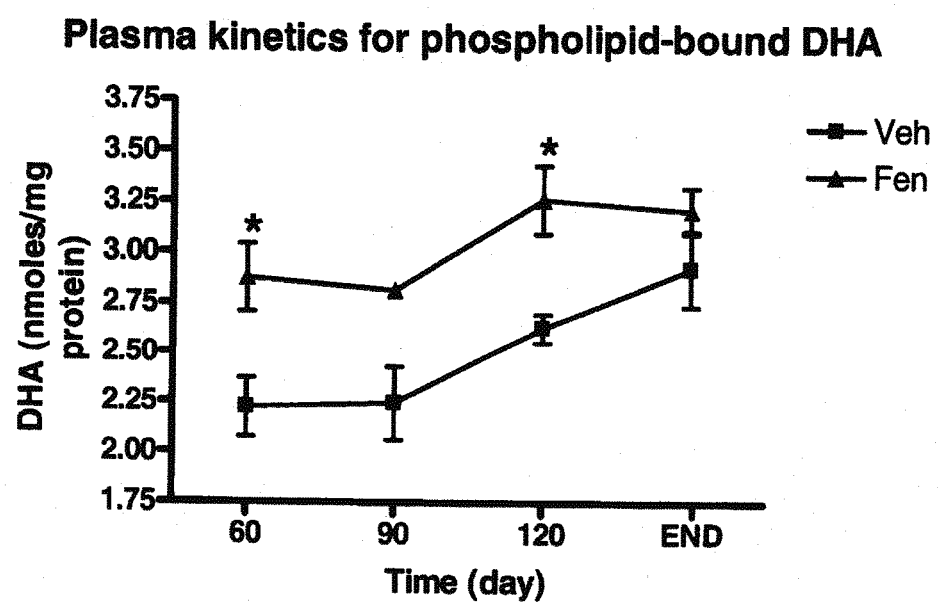
FIG. 18 shows the plasma kinetics for phospholipid-bound DHA. This graph displays the phospholipid-bound DHA concentration in mice treated with fenretinide (Fen, triangles) or vehicle (Veh, squares). Two-way ANOVA revealed a significant elevation in DHA levels in animals treated with fenretinide compared to vehicle-treated controls for the duration of the study (p≤0.0001). Bonferroni post-tests also revealed significantly higher DHA at both 60 and 120 days in fenretinide-treated mice. * signifies p≤0.05. n≈10 for each group.
Figure 19:
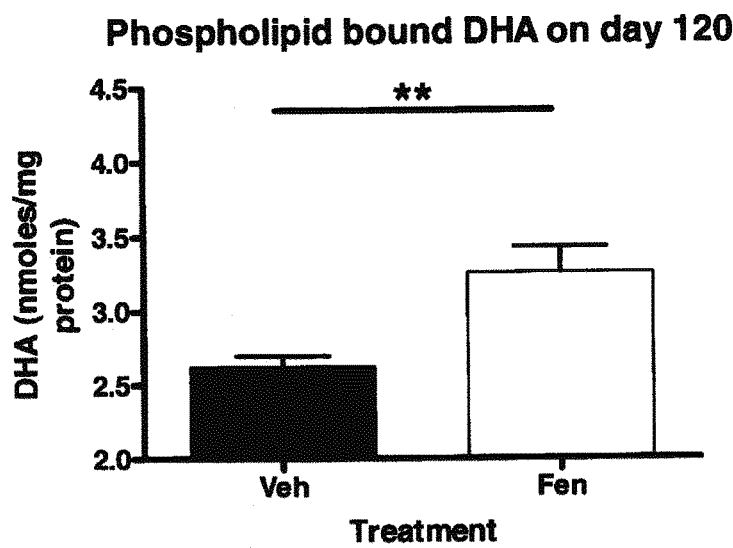
FIG. 19 shows plasma polyunsaturated fatty acids (PUFA) concentrations. PUFA levels were measured from plasma samples obtained 120 days after birth. Mice treated with 5 weekly doses of fenretinide (Fen) displayed significantly increased levels of phospholipid-bound omega-3 (ω-3) PUFA DHA (FIG. 19A), but significantly reduced levels of phospholipid-bound omega-6 (ω-6) PUFA AA (FIG. 19B), as compared to vehicle-treated controls (Veh). ** signifies p≤0.01. n=8 for both groups.
Figure 19:
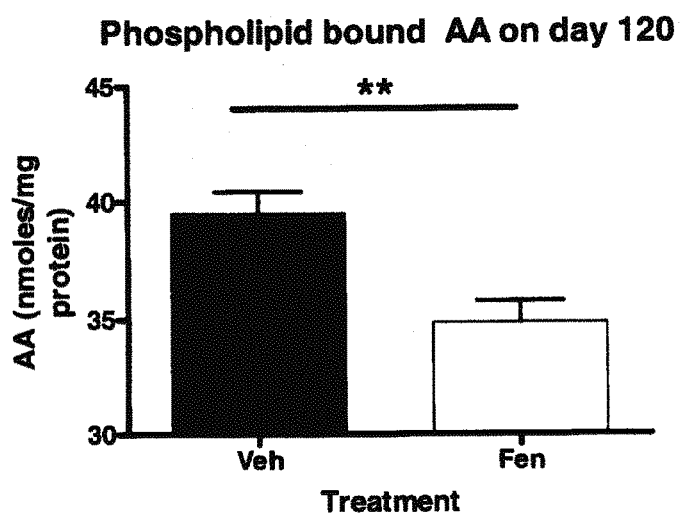

Effects of Fenretinide on Plasma Essential Fatty Acid (EFA) Profiles in SOD1$^{G93A}$ Transgenic Mice In order to determine the effect of treatment on systemic lipid profiles, plasma samples were collected at day 60, 90, 120 and at the clinical endpoint for both fenretinide-treated and control groups. Each sample was analyzed for the contribution of DHA, AA, MDA, NT and ceramides. Phospholipid-bound DHA levels were found to be significantly elevated in the plasma of fenretinide-treated animals compared to control mice. Significantly elevated DHA concentrations were detected for the duration of the experiment ($p \leq 0.0001$), shown in FIG. 18. In addition, significant increases in DHA were found independently at day 60 and 120 in fenretinide-treated mice. Treatment with fenretinide increased phospholipid-bound DHA at day 60 from 2.22±0.15 (n=9) from control animals to 2.88±0.18 (n=8), an increase of about 30% ($p \leq 0.05$). A similar increase (about 25%) was also observed at day 120 from 2.63±0.07 (n=8) for sham-treated mice to 3.26±0.17 (n=8) ($p \leq 0.01$) for the drug-treated group (FIGS. 18 and 19A). Phospholipid-bound AA, while slightly lower at 60 days of age in fenretinide-treated mice, only reached a statistically significant decline in samples taken on day 120, falling from 39.50±0.94 (n=8) for control mice to 34.87±0.91 (n=7) ($p \leq 0.01$) for the fenretinide treated group (a decrease of about 12%), as shown in FIG. 19B. Statistically significant differences in ceramide concentrations were not observed at any of the time points. Additionally, no significant differences in the levels of total fatty acids, phospholipid-bound AA or phospholipid-bound DHA were observed between vehicle-treated and fenretinide-treated groups when measured at the clinical endpoint. These results demonstrate that fenretinide treatment contributes to maintaining an environment of decreased ω-6 fatty acids while increasing ω-3 fatty acids.

Example 11

Figure 20:
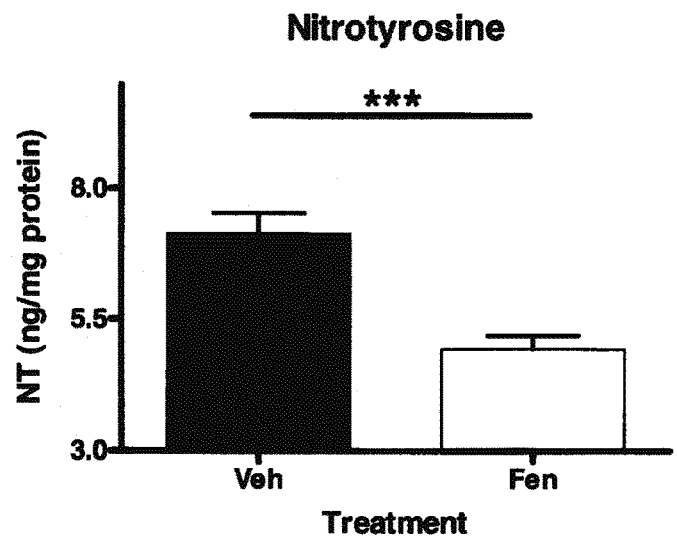
FIG. 20 shows the effect of fenretinide therapy on plasma lipid peroxidation/oxidative stress. Two markers of lipid peroxidation/oxidative stress, nitrotyrosine (NT, FIG. 20A) and malonyldialdehyde (MDA, FIG. 20B), were significantly decreased on day 120 in fenretinide-treated mice (Fen) compared to controls (Veh) in plasma samples measured at 120 days of age. *** signifies p≤0.001. n=7 or 8 for all groups.
Figure 20:
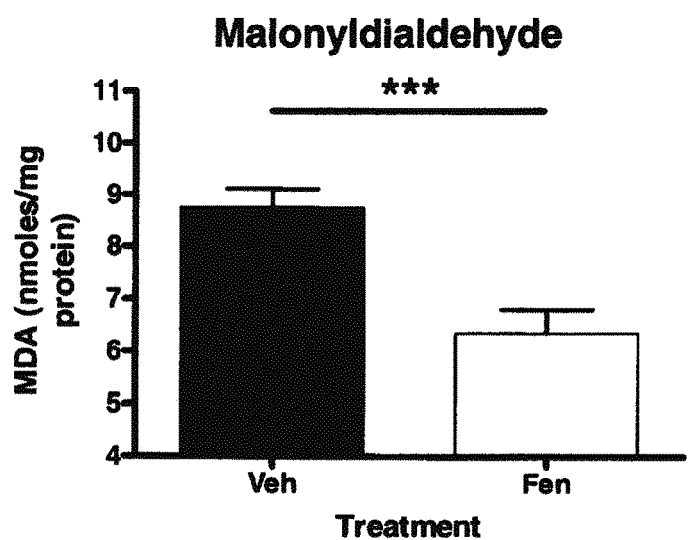

Effects of Fenretinide on Plasma Lipid Peroxidation and Oxidative Stress in SOD1$^{G93A}$ Transgenic Mice The samples tested for EFAs were also analyzed for the presence of two markers of lipid peroxidation/oxidative stress: nitrotyrosine (NT) and malonyldialdehyde (MDA). At 60 days of age fenretinide-treated mice had lower levels of NT, a difference that was statistically significant at day 120, at which point control animals possessed 45% higher levels of NT than mice treated with fenretinide ($p \leq 0.001$), as shown in FIG. 20A. MDA showed a similar profile becoming significantly (p=0.001) reduced by about 38% at 120 days of age in drug-treated mice (FIG. 20B). These results demonstrate that treatment with fenretinide is associated with a decrease in lipid peroxidation, and may thus provide protection from reactive oxygen and nitrogen species and oxidative stress, which are present at high levels in SOD1$^{G93A}$ mice.

Example 12

Figure 21:
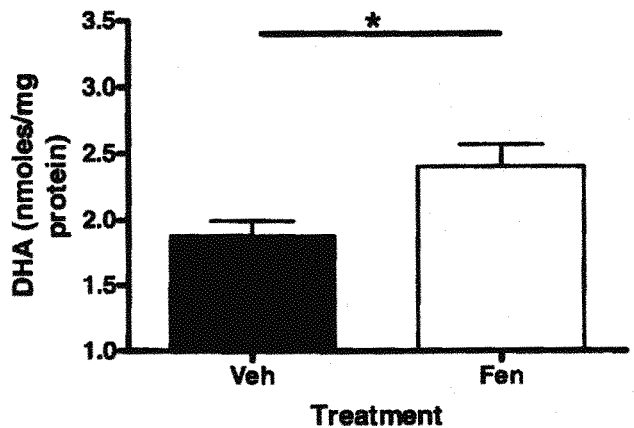
FIG. 21 shows PUFA concentrations in organs affected by ALS. (A) Phospholipid-bound DHA levels were significantly increased in the lumbar spinal cord of mice treated with fenretinide when compared to vehicle-treated controls. (B) A difference in AA from the same spinal cord samples was not detected. (C) Motor cortex samples revealed significantly lower levels of phospholipid-bound AA in fenretinide-treated mice. (D) DHA concentrations were higher in cortex samples derived from fenretinide-treated mice. * signifies p≤0.05. n=11 or 12 for all groups.
Figure 21:
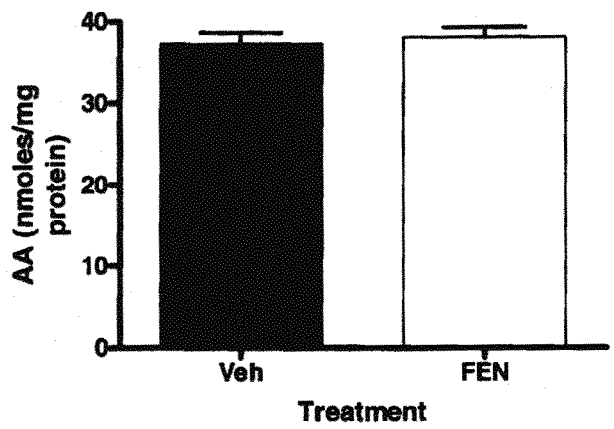
Figure 21:
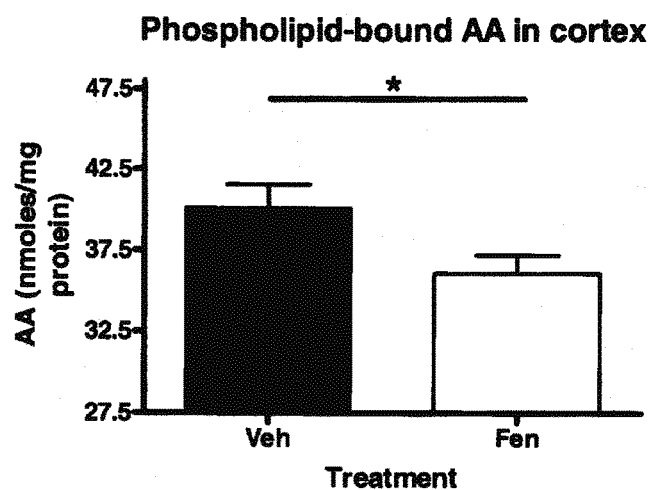
Figure 21:
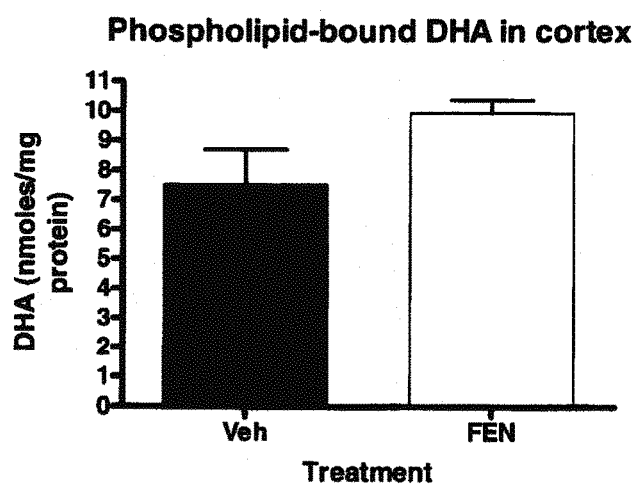

Effects of Fenretinide on EFA Profiles and Lipid Peroxidation/Oxidative Stress in ALS-affected Organs of SOD1$^{G93A}$ Transgenic Mice To establish whether the difference in plasma lipid profiles observed in plasma samples could also be observed in the organs directly affected by ALS, samples of lumbar spinal cord, brain stem and cerebral cortex were analyzed for the presence of the same lipid species and markers of lipid peroxidation. Samples were harvested when each animal reached the clinical endpoint. Neither AA nor DHA levels reached a significant difference between vehicle- and fenretinide-treated groups in the brain stem samples. AA in spinal cord samples and DHA in cortex samples were also not significantly affected by fenretinide treatment, as shown in FIGS. 21B and 21D, respectively, although DHA did show an increasing trend in the fenretinide-treated group (FIG. 21D). There was a statistically significant increase (about 28%) in phospholipid-bound DHA levels in the lumbar spinal cord of fenretinide-treated mice ($p \leq 0.05$), as shown in FIG. 21A. Also, phospholipid-bound arachidonic acid was roughly 10% lower in the cerebral cortex of fenretinide-treated animals ($p \leq 0.05$), as depicted in FIG. 21C. These results confirm that fenretinide treatment contributes to maintaining an environment of decreased ω-6 fatty acids while increasing ω-3 fatty acids, including in ALS-affected organs.

Example 13

Effects of Fenretinide on the Survival of Motor Neurons in SOD1$^{G93A}$ Transgenic Mice All histological preparations were derived from L4 spinal cord segments taken at 130 days of age. In order to quantify the number of surviving motor neurons, histological sections were stained with cresyl violet and the motor neurons of each ventral horn were counted by an individual blinded to the animal number and treatment conditions.

Figure 22:
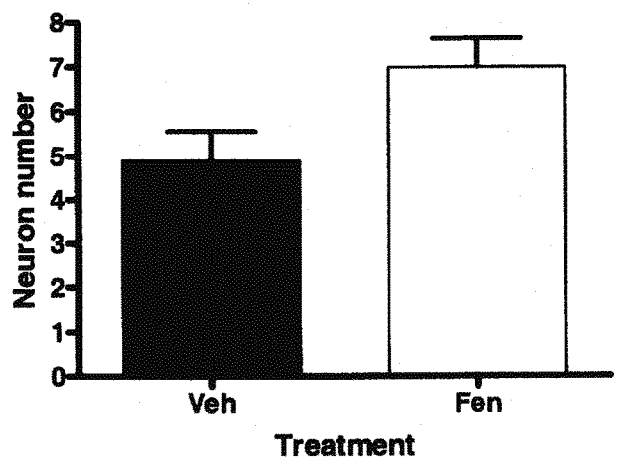
FIG. 22 shows the quantification of surviving motor neurons. (A) Motor neurons counted in the ventral horn of the 4$^{th}$ lumbar spinal cord segment appeared to be more numerous in mice treated with fenretinide. (B) Images depict motor neuron staining. Qualitative observations indicate that treated samples possessed more robust motor neurons. Arrows indicated alpha motor neurons identified in the ventral horn. n=4 for both groups.
Figure 22:
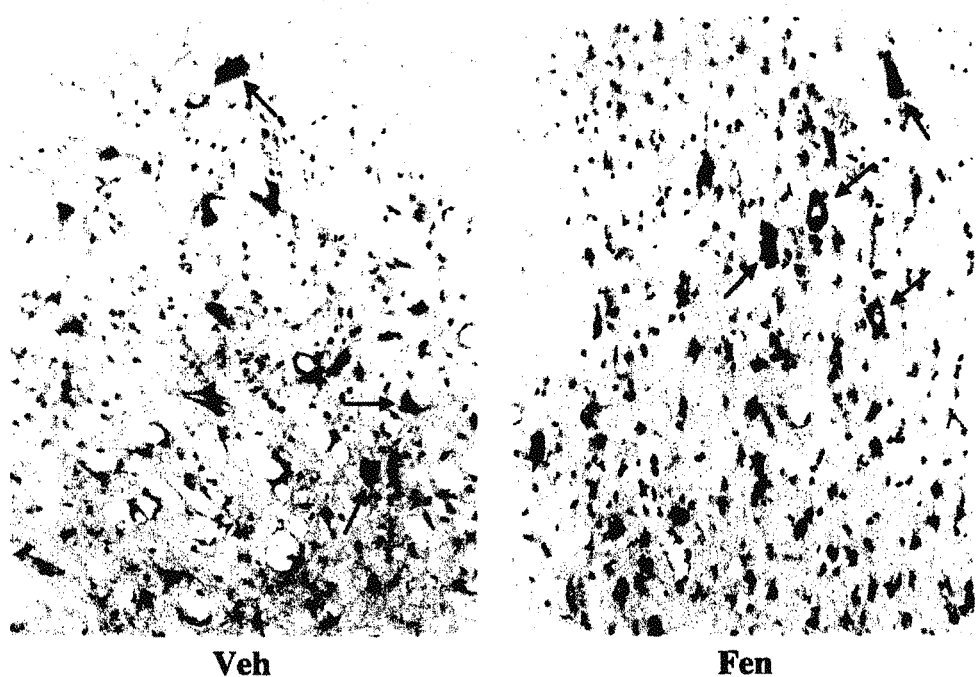

Representative images depicting motor neuron staining are shown in FIG. 22B. Counts were performed from both ventral horns on sections every 300 μm and an average of 4 sections (8 ventral horns) was taken for each animal. As shown in FIG. 22A, mice treated with fenretinide displayed approximately 20% to 30% more motor neurons than control mice.

Example 14

Effects of Fenretinide on Glial Activation in SOD1$^{G93A}$ Transgenic Mice

Figure 23:
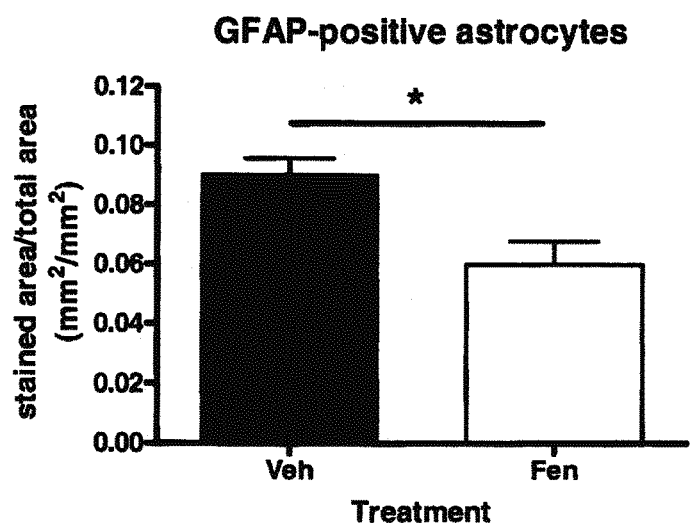
FIG. 23 shows the quantification of reactive gliosis. (A) GFAP-positive staining astrocytes occupied significantly less area of the 4$^{th}$ lumbar ventral horn in mice treated with fenretinide (Fen) compared to vehicle-treated (Veh) controls. (B) Qualitative observations reveal that spinal cords from vehicle-treated animals possess greater numbers of astrocytes and that these cells are more hypertrophic compared to samples from Fenretinide-treated mice. (C) Mac2-positive microglia were also significantly less numerous in fenretinide-treated mice. (D) Qualitative observations also revealed more numerous hypertrophic microglia in spinal cords from vehicle-treated mice. * signifies p≤0.05.
Figure 23:
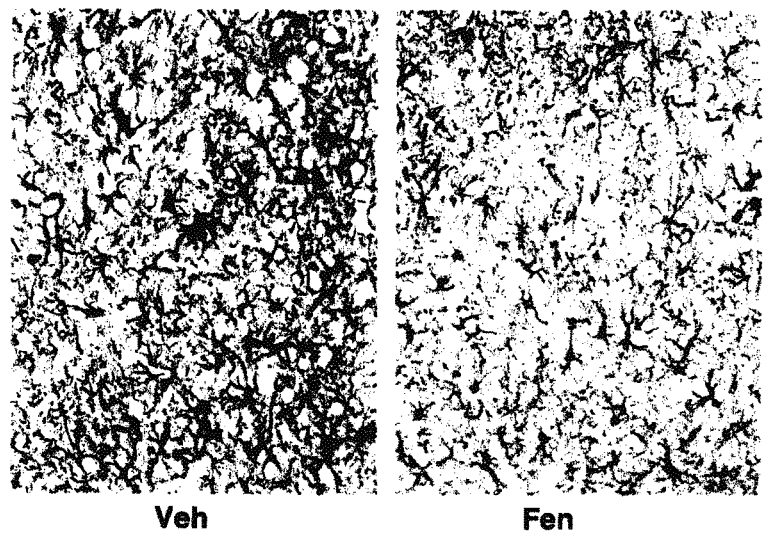
Figure 23:
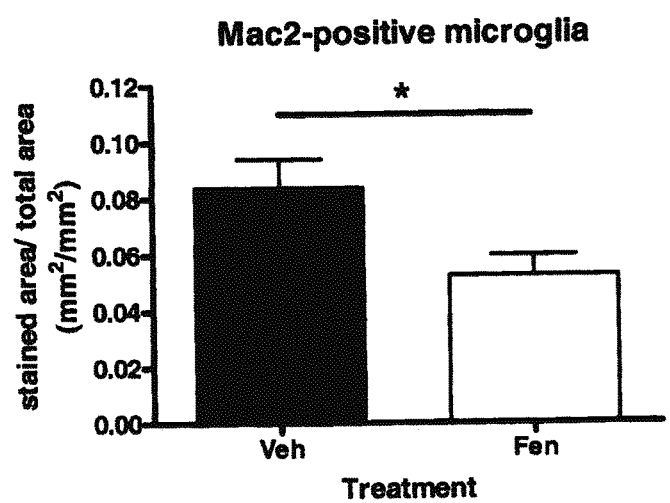
Figure 23:
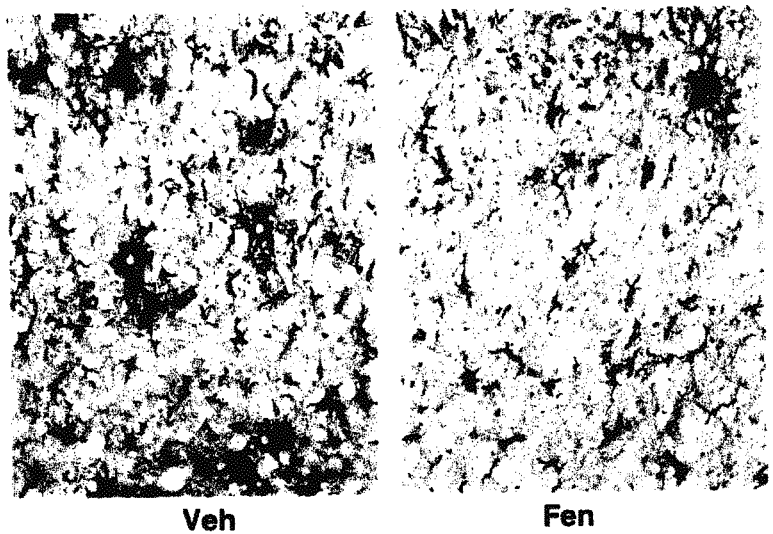

Immunohistochemistry was also performed on different serial sections from the same animals. Antibodies against both glial fibrillary acidic protein (GFAP), shown in FIG. 23B, and the Mac-2 antigen (Mac-2), shown in FIG. 23D, were used to identify activated astrocytes and microglia respectively. Images of both ventral horns were captured every 300 μm and imported into SigmaScan™ Pro image quantification software. The area occupied by darkly stained cells was quantified and normalized for the total area. As illustrated in FIG. 23A, analysis of GFAP-stained sections revealed that sham treated mice had more than 50% greater staining of the ventral horn then mice treated with fenretinide ($p \leq 0.05$). Mac-2 positive stained area was also significantly higher in control animals, with 60% more area stained ($p \leq 0.05$), as shown in FIG. 23C. It can be seen from the representative images in FIGS. 23B and 23D that vehicle-treated mice not only possessed a greater number of glial cells, but these cells displayed greater hypertrophy. These findings demonstrate that glial activation, a marker of CNS inflammation, is decreased in animals treated with fenretinide.

Although the present invention has been described hereinabove by way of specific embodiments thereof, it can be modified, without departing from the spirit and nature of the subject invention as defined in the appended claims.

What is claimed:

1. A method for treating spinal cord injury in a subject, said method comprising administering to said subject an effective amount of (i) fenretinide; (ii) a pharmaceutically-acceptable salt of fenretinide; or (iii) any combination of (i) and (ii).

2. The method according to claim 1, comprising administering to said subject an effective amount of fenretinide.

3. The method according to claim 1, wherein said method further comprises treatment or inhibition of a condition selected from (a) neural inflammation; (b) loss of neural cell or tissue; (c) increased neural arachidonic acid (AA) levels; (d) decreased neural docosahexaenoic acid (DHA) levels; (e) neural oxidative stress; and (f) any combination of (a) to (e).

4. The method according to claim 3, wherein said AA levels are phospholipid-bound AA levels.

5. The method according to claim 3, wherein said DHA levels are phospholipid-bound DHA levels.

6. The method according to claim 1, wherein said subject is a mammal.

7. The method according to claim 6, wherein said mammal is a human.

8. The method according to claim 2, wherein said method further comprises treatment or inhibition of a condition selected from (a) neural inflammation; (b) loss of neural cell or tissue; (c) increased neural arachidonic acid (AA) levels; (d) decreased neural docosahexaenoic acid (DHA) levels; (e) neural oxidative stress; and (f) any combination of (a) to (e).

9. The method according to claim 2, wherein said subject is a mammal.

10. The method according to claim 9, wherein said mammal is a human.

11. The method according to claim 1, wherein said administering improves locomotor function in said subject following said injury.

12. The method according to claim 2, wherein said administering improves locomotor function in said subject following said injury.

13. The method according to claim 1, wherein said administering reduces spinal cord tissue damage in said subject following said injury.

14. The method according to claim 2, wherein said administering reduces spinal cord tissue damage in said subject following said injury.

* * * * *